United States Patent [19]
Monroe et al.

[11] Patent Number: 5,625,049
[45] Date of Patent: Apr. 29, 1997

[54] NUCLEIC ACIDS ENCODING HUMAN ASTROVIRUS SEROTYPE 2

[76] Inventors: Stephan S. Monroe, 152 Poplar Cir., Decatur, Ga. 30030-3845; Roger I. Glass, 840 Springdale Rd., NE., Atlanta, Ga. 30306; Marion Koopmans, 750 Clifton Way, #3G; Baoming Jiang, 1422-B Druid Valley Dr., both of Atlanta, Ga. 30329

[21] Appl. No.: 61,465

[22] Filed: May 12, 1993

[51] Int. Cl.$^6$ .......................... C07H 21/02; C07H 21/04
[52] U.S. Cl. ...................... 536/23.72; 536/24.3
[58] Field of Search ............... 536/23.72, 24.3; 435/320.1

[56] References Cited

OTHER PUBLICATIONS

Sommer et al (Nucleic Acid Res 17:6749) 1989.
Embase No. 83104244 J. Hyg. 89/3: 539–540 (1982).
Wyn–Jones et al., Wat. Sci. Tech. 24: 285–290 (1991) "Growth of Clinical isolates of Astrovirus in a cell . . . ".
Young et al., P.N.A.S. 80: 1194–1198 (1983) "Efficient isolation of genes . . . ".
Herring et al., J. Gen. Virol. 53: 47–55 (1981) "Purification and characterization of Ovine . . . ".
Kurtz et al., Lancet 2:1405 (1984) "Human Astrovirus Serotypes".
Matsui et al., J. Virol 67:1712–1715 (1993) "Cloning and characterization of human astrovirus . . . ".
Willcocks et al., Epidermiol. Infect 107:405–410 (1991) "A dot–blot hybridization procedure . . . ".
Willcocks et al. Arch. Virol. 124:279–289 (1992) "The 3' terminal sequence of a human astrovirus".
Suzanne M. Matsui et al., "Cloning and Characterization of Human Astrovirus Immunoreactive Epitopes," *Journal of Virology,* 67(3):1712–1715 (Mar. 1993).
M.E. Major et al., "3' Terminal Nucleotide Sequence of Human Astrovirus Type 1 and Routine Detection of Astrovirus Nucleic Acid and Antigens," *Journal of Virological Methods,* 39:217–225 (1992).
M.M. Willcocks et al., "The 3' Terminal Sequence of a Human Astrovirus," *Arch. Virol.,* 124:279–289 (1992).
Stephan S. Monroe et al., "Temporal Synthesis Proteins and RNAs During Human Astrovirus Infection of Cultured Cells," *Journal of Virology,* 65(2):641–648 (Feb. 1991).
Stephan S. Monroe et al., "Human Astrovirus Serotype 2: cDNA Sequencing and Use of PCR for Detection in Clinical Specimens," *Third International Symposium on Positive Strand RNA Viruses,* Clearwater, Florida, Sep. 19–24, 1992.

*Primary Examiner*—W. Gary Jones
*Assistant Examiner*—Eggerton Campbell

[57] ABSTRACT

The present invention provides a nucleic acid encoding human Astrovirus serotype 2, or a unique fragment thereof. The sequence, a genomic RNA of human astrovirus serotype 2 contains 6,797 nucleotides, and is organized into three open reading frames. Also provided are purified antigenic polypeptide fragments encoded by the nucleic acid encoding human Astrovirus serotype 2, or unique portions thereof. The present invention also provides a monoclonal antibody specific for human astrovirus serotype 2 and isolated nucleic acids capable of selectively hybridizing with the nucleic acid of serotype 2, including methods for detecting the presence of serotype 2 utilizing these products.

8 Claims, 3 Drawing Sheets

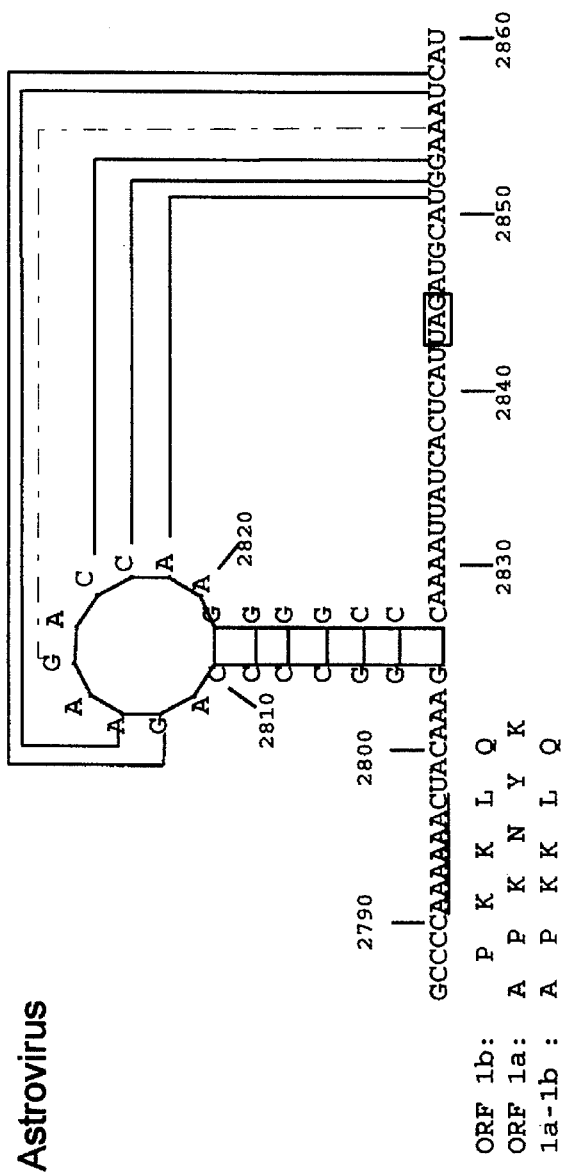
Fig. 2A Astrovirus
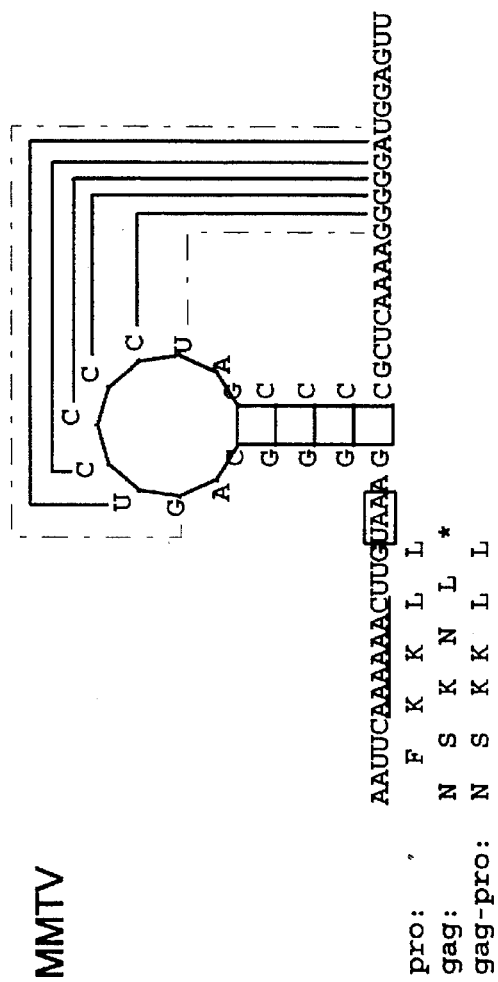
Fig. 2B MMTV

NUCLEIC ACIDS ENCODING HUMAN ASTROVIRUS SEROTYPE 2

BACKGROUND OF THE INVENTION

1. Field of the Invention

The present invention relates to astroviruses. In particular, the present invention relates to genomic and subgenomic nucleic acids of human astrovirus serotype 2.

2. Background Art

Astroviruses are 28-nm nonenveloped, viruses that were initially identified from the feces of infants with gastroenteritis by their distinctive ultrastructural features of characteristic five- or six-pointed surface stars (Appleton, J. et al., *Lancet*, 1: 1297 (1975); Madeley, C. R. et at., *Lancet*, 2: 451–452 (1975)). These nonenveloped agents were subsequently determined to be positive-strand RNA viruses (Herring, A. J. et al., *J. Gen. Virol.*, 53: 47 (1981); Monroe, S. S. et at., *J. Virol.*, 65: 641 (1991); Matsui, S. M. et al., *J. Virol.*, 67: 1712 (1993)). Immune electron microscopy and immunofluorescence techniques have now identified five serotypes of human astroviruses, currently designated H-Ast1 to H-Ast5 (Kurtz, J. B. et al., *Lancet*, 2: 1405 (1984)).

Astroviruses cause acute gastroenteritis in children and adults worldwide (Cruz, J. R. et al., *J. Clin. Microbiol.*, 30: 1140 (1992); Greenberg, H. B. et al., *Infect. Agents Dis.* 1: 71 (1992); Moe et al., *J. Clin. Microbiol*, 29: 2390 (1991)). However, the disease burden has been difficult to determine because of the lack of sensitive diagnostic assays. Recent studies have demonstrated that astroviruses were more frequently found in children with diarrhea than was previously thought (Herrmann et al., *J. Infect. Dis.* 161: 226 (1990); Herrmann et al., *N. Engl. J. Med.*, 324: 1757 (1991); Lew, J. F. et al., *J. Infect. Dis.*, 164: 673 (1991)). Outbreaks have been reported in kindergartens, (Konno, T. et al., *J. Med. Virol.*, 9: 11–17 (1982)) pediatric wards (Kurtz, J. B. et al., *J. Clin. Pathol.*, 30: 948–952 (1977)) and also in nursing homes (Gary, J. J. et al., *J. Med. Virol.*, 23: 377–381 (1987); Oshiro, L. S. et al., *J. Infect. Dis.*, 143: 791–795 (1981)).

Clinical signs associated with astrovirus infection include nausea, vomiting, non-bloody diarrhea, abdominal cramps, headaches, fever, chills and myalgia (LeBaron, C. W. et al., *Morbidity and Mortality Weekly Report* (Centers for Disease Control), Vol. 39 (Apr. 27, 1990)). Although most transmission is probably person-to-person among children, contaminated water and shellfish have also given rise to outbreaks in Britain (Kurtz, J. B. et at., (Ciba Foundation Symposium; 128), Chichester, UK: John Wiley & Sons Ltd., pp. 92–107 (1987)). Asymptomatic shedding of astrovirus has been documented (Ashley, C. R. et al., *J. Clin. Pathol.*, 31: 939–943 (1978)) and infectivity can last as long as two days after clinical symptoms (White, K. E. et at., *Am. J. Epidemiol.*, 124: 120–126 (1986)). Immuno-comprised individuals, e.g., AIDS patients, especially risk infection from astroviruses.

Previous studies of the biochemical properties of purified astrovirus particles have provided divergent results concerning the number and size of the proteins present in astroviruses; from two to as many as six polypeptides have been reported, ranging in size from 5.5 kDa to 42 kDa (Willcocks, M. M. et al., *Rev. Med. Virol.*, 2: 97–106 (1992)). Likewise, there have been conflicting reports of the presence of subgenomic RNA present in astroviruses (Monroe, S. S. et al., *J. of Virol.*, 65(2): 641–648 (1991); Willcocks et al., *Arch. Virol.*, 124: 279–289 (1992). Moreover, characterization of the genome has been hindered because of the fastidious growth of astroviruses in vitro.

Investigators have reported partial sequence information from internal regions and at the 3' end of human astrovirus serotype 1 (H-Ast1) including: 1034 nucleotides from the 3' end of genomic RNA, (Willcocks, M. M. et al., *Arch. Virol.*, 124: 279–289 (1992)) a 289 nucleotide immunoreactive epitope which overlaps the 3' end sequence (Matsui, S. M. et al., *J. of Virol.*, 67: 1712–1715 (1993)), and two overlapping regions which hybridize only to genomic RNA (Matsui, S. M. et al. (1993)).

The fastidious nature of the virus coupled with extremely low levels of viral RNA generated by the organism during growth have made conventional sequencing approaches unpredictable and unreliable. Thus, despite a great need, the art has yet to provide sequences for human astrovirus type 2. The present invention satisfies this need by utilizing a unique combination of sequencing techniques to identify, diagnose, and treat astrovirus infection by providing nucleotide sequences for the complete genomic and subgenomic RNA of serotype 2 (H-Ast2) and analysis of the entire genomic RNA of H-Ast2. The present invention also provides the surprising discovery of a ribosomal frame shift occurring in one open reading frame which results in encoding of a fusional nonstructural polyprotein.

SUMMARY OF THE INVENTION

The present invention provides a nucleic acid encoding human Astrovirus serotype 2, or a unique fragment thereof. The sequence for the genomic RNA of human astrovirus was sequenced from virion RNA and cDNA and was found to contain 6797 nucleotides, exclusive of the poly A tail, organized into three open reading frames (defined as Open Reading Frames (ORFs) 1a, 1b, and 2)). A ribosomal frameshift site is identified in the overlap region of ORFs 1a and 1b at position 2794. This translation frameshift results in the suppression of in-frame amber termination at the end of ORF 1a and the synthesis of a nonstructural, fusion polyprotein that contains the putative protease and RNA-dependent RNA polymeruse.

The present invention also provides the sequence of a nucleic acid encoding a subgenomic RNA of human Astrovirus serotype 2. This 2484-nucleotide RNA contains a single open reading frame, which encodes a protein with a molecular mass of about 88 kDa.

The present invention provides purified antigenic polypeptide fragments encoded by the nucleic acid encoding human Astrovirus serotype 2. In particular, the present invention provides a purified antigenic polypeptide fragment encoded by the nucleic acid encoding open reading frame 2, or a unique portion thereof, in a pharmaceutically acceptable carrier.

The present invention also provides isolated nucleic acids capable of selectively hybridizing with the nucleic acid of human Astrovirus serotype 2 including, but not limited to, primers and probes for utilization in polymerase chain reaction (PCR) and other nucleic acid amplification techniques.

Further, the present invention provides vectors comprising the nucleic acid encoding human astrovirus serotpye 2 or a unique fragment thereof and provides the vector in a host capable of expressing the polypeptide encoded by that nucleic acid.

Finally, the present invention also provides a purified monoclonal antibody specifically reactive with human Astrovirus serotype 2 and a method of detection of human Astrovirus serotype 2 utilizing the antibodies of the present invention.

BRIEF DESCRIPTION OF THE DRAWINGS

FIG. 2 shows (A) Nucleotide sequence and predicted RNA secondary structure in the overlap region of astrovirus ORFs 1a and 1b. The putative frameshift site ("shifty" heptanucleotide sequence) is underlined and the termination codon for ORF1a is boxed. The RNA secondary structure was predicted using the RNAFOLD program (Zuker, M. et al., (1981)). A potential pseudoknot structure was predicted by searching the region downstream of the stem-loop structure for sequences complementary to the loop sequence. Three base pairs may be sufficient for the pseudoknot formation (Pleij, C. W. A. et al., Trends Blochem. Sci, 16: 143 (1990)) but the formation of a larger "secondary" stem with a non-canonical G-A pair (shown by a dotted line) and two additional canonical base pairs is also possible. The deduced amino acid sequences of ORFs 1a, 1b, and 1a–1b surrounding the frameshift site are shown.

(B) Nucleotide sequence and predicted RNA secondary structure in the gag-pro overlap region of MMTV (Jacks, T. et al., Cell, 55: 447 (1988); Hatfield, D. L. et al., Trends Biochem. Sci., 15: 186 (1990); Chamorro, M. et al., Proc. Natl. Acad. Sci. USA, 89: 713–717 (1992)) are shown for comparison. The frameshift site, the termination codon, and the RNA pseudoknot are indicated or described as in (A).

Figure 3:
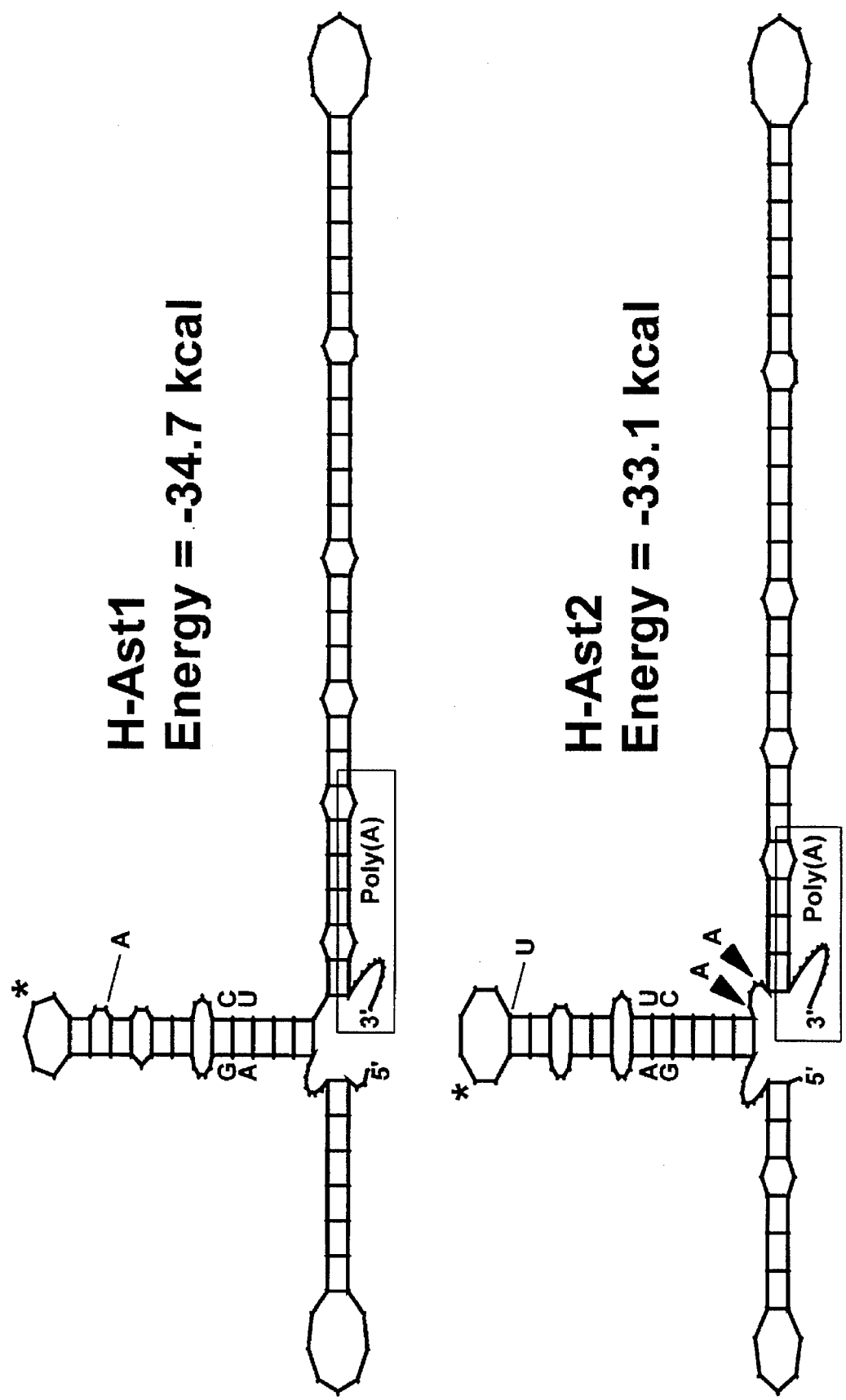

FIG. 3 shows the predicted secondary structure at the 3' end of astrovirus RNA sequences. The structures were calculated by the method of Zuker and Stiegler (Zuker, M. et al., Nucleic Acids Res., 9: 133–148 (1981)). The H-Ast1 structure contains a total of 154 nucleotides including 134 bases from the reported 3'-end sequence (Willcocks, M. M. et al., Arch. Virol., 124: 279–289 (1992)) plus 20 additional adenine residues. The H-Ast2 structure contains 156 nucleotides corresponding to bases 2349 to 2504 in SEQ ID NO: 3. The region of the poly(A) tract involved in stem I is outlined with a box. The two insertions in the loop between stems I and II are shown with arrowheads. The residues within the conserved stem II that vary between the two serotypes are indicated. The terminator codons, in the loop of stem II, are marked with asterisks.

DETAILED DESCRIPTION OF THE INVENTION

The present invention may be understood more readily by reference to the following detailed description of specific embodiments and the Examples included therein.

As used in the claims, "a" can mean one or more.

The present invention provides an isolated nucleic acid encoding human Astrovirus serotype 2 as set forth in the Sequencing Listing as SEQ ID NO: 1, or a unique fragment thereof. The invention also provides a nucleic acid capable of selectively hybridizing the DNA, RNA and cDNA sequences which can be derived from SEQ ID NO: 1. While SEQ ID NO: 1 is an RNA sequence, the invention also provides the corresponding DNA sequence.

By "isolated" is meant identifiably separated from other nucleic acids found in the naturally occurring organism. By "capable of selectively hybridizing" is meant a sequence which does not hybridize with other nucleic acids to prevent an adequate positive hybridization with nucleic acids from human Astrovirus serotype 2. By "unique fragment" is meant a fragment can selectively hybridize with a RNA, DNA or eDNA sequence derived from the novel sequences.

An example of such a nucleic acid is an open reading frame of 2,387 bases comprising nucleotides 4,325 through 6,712 (designated open reading frame 2 (ORF 2)) as set forth in SEQ ID NO: 1. This specific nucleic acid can be used to detect human astrovirus serotype 2 in methods such as polymerase chain reaction, ligase chain reaction and hybridization. Alternatively, the ORF 2 sequence can be utilized to produce an antigentic protein or protein fragment.

In addition, the nucleic acid can be utilized to find sequences homologous with nucleotide sequences present in other human or animal astroviruses. Such an amino acid sequence shared with other astroviruses can be used for example to simultaneously detect related strains or as a basis for a multiprotective vaccine.

An isolated nucleic acid capable of selectively hybridizing with or selectively amplifying a nucleic acid encoding the human Astrovirus serotype 2, or unique fragments thereof is also contemplated. The sequences can be selected based on the nucleotide sequence and the utility of the particular sequence.

Modifications to the nucleic acids of the invention are also contemplated as long as the essential structure and function of the polypeptide encoded by the nucleic acids is maintained. Likewise, fragments used as primers or probes can have substitutions so long as enough complementary bases exist for selective hybridization (Kunkel et al. Methods Enzmol. 1987: 154–367, 1987).

In one embodiment the present invention provides, an isolated nucleic acid encoding open reading frame 1a of human Astrovirus serotype 2, comprising nucleotides 83 through 2,842 contained in the nucleotide sequence as set forth in the Sequencing Listing SEQ ID NO: 1, or a unique fragment thereof. The open reading frame designated "1a" is defined as comprising nucleotides 83 through 2,842 contained in the nucleotide sequence set forth in the Sequencing Listing SEQ ID NO: 1 and depicted in FIG. 1. Also contemplated by the present invention is an isolated nucleic acid capable of selectively hybridizing with the nucleic acid encoding open reading frame 1a.

In another embodiment, the present invention provides an isolated nucleic acid encoding open reading frame 1b of human Astrovirus serotype 2, comprising nucleotides 2,773 through 4,329 contained in the nucleotide sequence as set forth in the Sequencing Listing SEQ ID NO: 1, or a unique fragment thereof. The open reading frame designated "1b" is defined as comprising nucleotides 2,773 through 4,329 contained in the nucleotide sequence set forth in the Sequencing Listing SEQ ID NO: 1 and depicted in FIG. 1. Also contemplated by the present invention is an isolated nucleic acid capable of selectively hybridizing with the nucleic acid encoding open reading frame 1b.

Another embodiment of the present invention provides an isolated nucleic acid encoding open reading frame 2 of human Astrovirus serotype 2, comprising nucleotides 4,325 through 6,712 contained in the nucleotide sequence as set forth in the Sequencing Listing as SEQ ID NO: 1, or a unique fragment thereof. The open reading frame designated "2" is defined as comprising nucleotides 4,325 through 6,712 contained in the nucleotide sequence set forth in the Sequencing Listing SEQ ID NO: 1 and depicted in FIG. 1. Also contemplated by the present invention is an isolated nucleic acid capable of selectively hybridizing with the nucleic acid encoding open reading frame 1b.

The present invention also provides an isolated nucleic acid encoding open reading frame 1a/1b of human astrovirus serotype 2, as set forth in the nucleotide sequence defined in the Sequencing Listing as SEQ ID NO: 2, or a unique fragment thereof. A minus 1 frame shift occurs at position 2,712 of the sequence depicted in SEQ ID NO: 2. The open reading frame 1a/1b can also be identified in FIG. 1 and in SEQ ID NO: 1 wherein it comprises nucleotides 83, through 4,329. The minus 1 frameshift occurs at position 2,794 of the sequence depicted in SEQ ID NO: 1. Also contemplated by the present invention is an isolated nucleic acid capable of selectively hybridizing with the nucleic acid encoding open reading frame 1a/1b.

In another embodiment, the present invention provides an isolated nucleic acid encoding a subgenomic RNA of human Astrovirus serotype 2, as set forth in the nucleotide sequence defined in the Sequencing Listing as SEQ ID NO: 3, or a unique fragment thereof. The subgenomic RNA of human Astrovirus serotype 2 can also be identified in FIG. 1 and in SEQ ID NO: 1 wherein it comprises nucleotides 4,314 through 6,797 exclusive of the polyA tail. Also contemplated by the present invention is an isolated nucleic acid capable of selectively hybridizing with the nucleic acid encoding the subgenomic RNA of human Astrovirus serotype 2. While the nucleic acids can be derived as set forth in the examples, given the sequences, it is also possible to synthesize partial sequences and enzymatically combine the partial sequences to make an entire synthetic gene.

Also provided are purified antigenic polypeptides encoded by the nucleic acids. The invention also provides these antigenic polypeptides in a pharmaceutically acceptable carrier. The amino acid sequence of these polypeptides can be deduced from the nucleotide sequences set forth in the Sequence Listing. One example is set forth is SEQ ID NO: 4.

Purified antigenic polypeptide fragments encoded by the nucleic acids of the present invention are also contemplated. As used herein, "purified" means the antigen is at least sufficiently free of contaminants or cell components with which the antigen normally occurs to distinguish the antigen from the contaminants or components. Purified human Astrovirus serotype 2 antigen and antigenic fragments thereof of the present invention are also referred to herein as "the antigen" or "the H-Ast-2 antigen." It is contemplated that the antigenic fragments can be encoded from any portion of the nucleic acid encoding human Astrovirus serotype 2 as set forth in SEQ ID NO: 1, but especially from fragments encoded by the open reading frames 1a,1b,1a/1b, and 2 as described herein.

Specifically, one example provides an approximately 88 kDa antigenic polypeptide encoded by an open reading frame of 2,387 bases (ORF 2) consisting essentially of the amino acids encoded by nucleotides 4,325 through 6,712 contained in the nucleotide as sequence set forth in the Sequence Listing as SEQ ID NO: 1.

An antigenic fragment of the antigen can be isolated from the whole antigen by chemical or mechanical disruption. The purified fragments thus obtained can be tested to determine their antigenieity and specificity by the methods taught herein. Antigenic fragments of the antigen can also be synthesized directly. An immunoreactive fragment is generally an amino acid sequence of at least about five consecutive amino acids derived from the antigen amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologous to immunoreactive regions of the antigen and to modify these fragments by inclusion, deletion or modification of particular amino acids residues in the derived sequences. Thus, synthesis or purification of an extremely large number of peptides derived from the antigen is possible.

The amino acid sequences of the present polypeptides can contain an immunoreactive portion of the H-Ast-2 antigen attached to sequences designed to provide for some additional property, such as solubility. The amino acid sequences of an H-Ast-2 antigen can include sequences in which one or more amino acids have been substituted with another amino acid to provide for some additional property, such as to remove/add amino acids capable of disulfide bonding, to increase its bio-longevity, alter enzymatic activity, or alter interactions with gastric acidity. In any case, the peptide must posses a bioactive property, such as immunoreactivity, immunogenicity, etc.

The purified polypeptide fragments thus obtained can be tested to determine their immunogenicity and specificity. Briefly, various concentrations of a putative immunogenically specific fragment are prepared and administered to an animal and the immunological response (e.g., the production of antibodies or cell mediated immunity) of an animal to each concentration is determined. The amounts of antigen administered depend on the subject, e.g. a human or a guinea pig, the condition of the subject, the size of the subject, etc. Thereafter an animal so inoculated with the antigen can be exposed to the virus to test the potential vaccine effect of the specific immunogenic fragment. The specificity of a putative immunogenic fragment can be ascertained by testing sera, other fluids or lymphocytes from the inoculated animal for cross reactivity with other closely related Astroviruses.

A vector comprising the nucleic acids of the present invention is also provided. The vectors of the invention can be in a host capable of expressing the antigenic polypeptide fragments contemplated by the present invention.

There are numerous *E. coli* expression vectors known to one of ordinary skill in the art useful for the expression of the antigen Other microbial hosts suitable for use include bacilli, such as *Bacillus subtilis*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system from phage lambda. The promoters will typically control expression, optionally with an operator sequence, and have ribosome binding site sequences for example, for initiating and completing transcription and translation. If necessary an amino terminal methionine can be provided by insertion of a Met codon 5' and in-frame with the antigen. Also, the carboxyterminal extension of the antigenic fragments can be removed using standard oligonucleotide mutagenesis procedures.

Additionally, yeast expression can be used. There are several advantages to yeast expression systems. First, evidence exists that proteins produced in a yeast secretion systems exhibit correct disulfide pairing. Second, post-translational glycosylation is efficiently carried out by yeast secretory systems. The *Saccharomyces cerevisiae* pre-pro-alpha-factor leader region (encoded by the MFα-1 gene) is routinely used to direct protein secretion from yeast (Brake et al.,1984). The leader region of pre-pro-alpha-factor contains a signal peptide and a pro-segment which includes a recognition sequence for a yeast protease encoded by the KEX2 gene: this enzyme cleaves the precursor protein on the carboxyl side of a Lys-Arg dipeptide cleavage-signal sequence. The antigen coding sequence can be fused in-frame to the pre-pro-alpha-factor leader region. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or β-galactosidase, used to facilitate purification of the fusion protein by affinity chromatography. The insertion Of protease cleavage sites to separate the components of the fusion protein is applicable to constructs used for expression in yeast.

Mammalian cells permit the expression of proteins in an environment that favors important post-translational modifications such as folding and cysteine pairing, addition of complex carbohydrate structures, and secretion of active protein. Vectors useful for the expression of antigen in mammalian cells are characterized by insertion of the antigen coding sequence between a strong viral promoter and a polyadenylation signal. The vectors can contain genes conferring either gentamicin or methotrexate resistance for use as selectable markers. The antigen and immunoreactive fragment coding sequence can be introduced into a Chinese hamster ovary cell line using a methotrexate resistance-encoding vector. Presence of the vector DNA in transformed cells can be confirmed by Southern analysis and production of a cDNA or opposite strand RNA corresponding to the antigen coding sequence can be confirmed by northern analysis. A number of other suitable host cell lines capable of secreting intact human proteins have been developed in the art, and include the CHO cell lines, HeLa cells, myeloma cell lines, Jurkat cells, etc. Expression vectors for these cells can include expression control sequences, such as an origin of replication, a promoter, an enhancer, and necessary information processing sites, such as ribosome binding sites, RNA splice sites, polyadenylation sites, and transcriptional terminator sequences. Preferred expression control sequences are promoters derived from immunoglobulin genes, SV40, Adenovirus, Bovine Papilloma Virus, etc. The vectors containing the nucleic acid segments of interest can be transferred into the host cell by well-known methods, which vary depending on the type of cellular host. For example, calcium chloride transfection is commonly utilized for prokaryotic cells, whereas calcium phosphate treatment or electroporation may be used for other celluar hosts.

Alternative vectors for the expression of antigen in mammalian cells, those similar to those developed for the expression of human gammainterferon, tissue plasminogen activator, clotting Factor VIII, hepatitis B virus surface antigen, protease Nexinl, and eosinophil major basic protein, can be employed. Further, the vector can include CMV promoter sequences and a polyadenylation signal available for expression of inserted nucleic acid in mammalian cells (such as COS7).

The nucleic acid sequences can be expressed in hosts after the sequences have been operably linked to, i.e., positioned to ensure the functioning of, an expression control sequence. These expression vectors are typically replicable in the host organisms either as episomes or as an integral part of the host chromosomal DNA. Commonly, expression vectors can contain selection markers, e.g., tetracycline resistance or hygromycin resistance, to permit detection and/or selection of those cells transformed with the desired nucleic acid sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

A purified monoclonal antibody specifically reactive with human Astrovirus serotype 2 is also provided. The antibodies can be specifically reactive with a unique epitope of the antigen or they can also react with epitopes of other organisms. The term "reactive" means capable of binding or otherwise associating nonrandomly with an antigen "Specifically reactive" as used herein deserves an antibody or other ligand that does not cross react substantially with any antigen other than the one specified, in this case, human Astrovirus serotype 2. Antibodies can be made as described in the Examples (see also, Harlow and Lane, *Antibodies; A Laboratory Manual*, Cold Spring Harbor Laboratory, Cold Spring Harbor, N.Y., 1988). Briefly purified antigen can be injected into an animal in an amount and in intervals sufficient to elicit an immune response. Antibodies can either be purified directly, or spleen cells can be obtained from the animal. The cells are then fused with an immortal cell line and screened for antibody secretion. The antibodies can be used to screen clone libraries for cells secreting the antigen Those positive clones can then be sequenced (see, for example, Kelly et al., *Bio/Technology*, 10: 163–167, (1992) and Bebbington et at., *Bio/Technology*, 10: 169–175,(1992).

The antibody can be bound to a substrate or labeled with a detectable moiety or both bound and labeled. The detectable moieties contemplated with the composition of the present invention are those listed below in the description of the diagnostic methods, including fluorescent, enzymatic and radioactive markers.

A purified human Astrovirus serotype 2 antigen bound to a substrate and a ligand specifically reactive with the antigen are also contemplated. Such a purified ligand specifically reactive with the antigen can be an antibody. The antibody can be a monoclonal antibody obtained by standard methods and as described herein. The monoclonal antibody can be secreted by a hybridoma cell line specifically produced for that purpose (Harlow and Lane, 1988). Likewise, nonhuman polyclonal antibodies specifically reactive with the antigen are within the scope of the present invention. The polyclonal antibody can also be obtained by the standard immunization and purification protocols (Harlow and Lane, 1988).

The present invention provides a method of detecting the presence of human Astrovirus serotype 2 in a subject, comprising the steps of contacting an antibody-containing sample from the subject with a detectable mount of the antigenic polypeptide fragment of the present invention and detecting the reaction of the fragment and the antibody, the reaction indicating the presence of the Astrovirus or a previous infection with H-Ast 2.

One example of the method of detecting human Astrovirus serotype 2 is performed by contacting a fluid or tissue sample from the subject with an amount of a purified antibody specifically reactive with the antigen as defined herein, and detecting the reaction of the ligand with the antigen. It is contemplated that the antigen will be on intact cells containing the antigen, or will be fragments of the antigen. As contemplated herein, the antibody includes any ligand which binds the antigen, for example, an intact antibody, a fragment of an antibody or another reagent that has reactivity with the antigen. The fluid sample of this method can comprise any body fluid which would contain the antigen or a cell containing the antigen, such as blood, plasma, serum, saliva, feces and urine. Other possible examples of body fluids include sputum, mucus, gastric juice and the like.

Enzyme immunoassays such as immunofluorescence assays (IFA), enzyme linked immunosorbent assays (ELISA) and immunoblotting can be readily adapted to accomplish the detection of the antigen An ELISA method effective for the detection of the antigen can, for example, be as follows: (1) bind the antibody to a substrate; (2) contact the bound antibody with a fluid or tissue sample containing the antigen; (3) contact the above with a secondary antibody bound to a detectable moiety (e.g., horseradish peroxidase enzyme or alkaline phosphatase enzyme); (4) contact the above with the substrate for the enzyme; (5) contact the above with a color reagent; (6) observe color change. The above method can be readily modified to detect antibody as well as antigen.

Another immunologic technique that can be useful in the detection of H-Ast 2 or previous H-Ast 2 infection utilizes monoclonal antibodies (MAbs) for detection of antibodies specifically reactive with H-Ast 2 antigen Briefly, sera or other body fluids from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

A micro-agglutination test can also be used to detect the presence of H-Ast 2 in a subject. Briefly, latex beads (or red blood cells) are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or capable of being detected by a spectrophotometer. In a modification of the above test, antibodies specifically reactive with the antigen can be bound to the beads and antigen in the tissue or body fluid thereby detected.

In addition, as in a typical sandwich assay, the antibody can be bound to a substrate and reacted with the antigen Thereafter, a secondary labeled antibody is bound to epitopes not recognized by the first antibody and the secondary antibody is detected. Since the present invention provides H-Ast-2 antigen for the detection of infectious, H-Ast 2 or previous H-Ast 2 infection other serological methods such as flow cytometry and immunoprecipitation can also be used as detection methods.

In the diagnostic methods taught herein, the antigen can be bound to a substrate and contacted by a fluid sample such as serum, urine, saliva, feces or gastric juice. This sample can be taken directly from the patient or in a partially purified form. In this manner, antibodies specific for the antigen (the primary antibody) will specifically react with the bound antigen Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecific ally with, the ligand or reacted antibody, will be selected for its ability to react with multiple sites on the primary antibody. Thus, for example, several molecules of the secondary antibody can react with each primary antibody, making the primary antibody more detectable.

The detectable moiety will allow visual detection of a precipitate or a color change, visual detection by microscopy, or automated detection by spectrometry, radiometric measurement or the like. Examples of detectable moieties include fluorescein and rhodamine (for fluorescence microscopy), horseradish peroxidase (for either light or electron microscopy and biochemical detection), biotin-streptavidin (for light or electron microscopy) and alkaline phosphatase (for biochemical detection by color change). The detection methods and moieties used can be selected, for example, from the list above or other suitable examples by the standard criteria applied to such selections (Harlow and Lane, 1988).

The antigen, e.g., a purified antigenic polypeptide fragment encoded by open reading frame 2 of this invention can be used in the construction of a vaccine comprising an immunogenic mount of the antigen and a pharmaceutically acceptable carrier. The vaccine can be the entire antigen, the antigen on an intact H-Ast 2 organism, *E. coli* or other strain, or an epitope specific to the antigen The vaccine can also be potentially cross-reactive with antibodies to other antigens. The vaccine can then be used in a method of preventing diarrhea or other complications of H-Ast 2 infection.

Immunogenic amounts of the antigen can be determined using standard procedures. Briefly, various concentrations of a putative specific immunoreactive epitope are prepared, administered to an animal and the immunological response (e.g., the production of antibodies) of an animal to each concentration is determined.

The pharmaceutically acceptable carrier can comprise saline or other suitable carriers (Arnon, R. (Ed.) *Synthetic Vaccines I*: 83–92, CRC Press, Inc., Boca Raton, Fla., 1987). An adjuvant can also be a part of the carrier of the vaccine, in which case it can be selected by standard criteria based on the antigen used, the mode of administration and the subject (Arnon, R. (Ed.), 1987). Methods of administration can be by oral or sublingual means, or by injection, depending on the particular vaccine used and the subject to whom it is administered.

It can be appreciated from the above that the vaccine can be used as a prophylactic or a therapeutic modality. Thus, the invention provides methods of preventing or treating H-Ast 2 infection and the associated diseases by administering the vaccine to a subject.

The presence of H-Ast 2 can also be determined by detecting the presence of a nucleic acid specific for H-Ast 2 or the antigens of H-Ast 2 encoded by the nucleic acid. The present invention provides a method of detecting the presence of human Astrovirus serotype 2 in a subject, comprising detecting the presence of the nucleic acid encoding human Astrovirus serotype 2. The specificity of these sequences for H-Ast 2 can be determined by conducting a computerized comparison with known sequences, catalogued in GenBank, a computerized database, using the computer programs Word Search or FASTA of the Genetics Computer Group (Madison, Wis.), which search the catalogued nucleotide sequences for similarities to the nucleic acid in question.

The nucleic acid specific for H-Ast 2 can be detected utilizing a nucleic acid amplification technique, such as polymerase chain reaction or ligase chain reaction. Alternatively, the nucleic acid is detected utilizing direct hybridization or by utilizing a restriction fragment length polymorphism. For example, the present invention provides a method of detecting the presence of H-Ast 2 comprising ascertaining the presence of a nucleotide sequence associated with a restriction endonuclease cleavage site. In addition, PCR primers which hybridize only with nucleic acids specific for H-Ast 2 can be utilized. The presence of amplification indicates the presence of H-Ast 2 sequence. In another embodiment a restriction fragment of a nucleic acid sample can be sequenced directly using, techniques known in the art and described herein and compared to the known unique sequence to detect H-Ast 2. In a further embodiment, the present invention provides a method of detecting the presence of H-Ast 2 by selective amplification by the methods described herein. In yet another embodiment HAst 2 can be detected by directly hybridizing the unique sequence with a H-Ast 2 selective nucleic acid probe. Furthermore, the nucleotide sequence could be amplified prior to hybridization by the methods described above.

Alternative probing techniques, such as ligase chain reaction (LCR), involve the use of mismatch probes, i.e., probes which are fully complementary with the target except at the point of the mutation. The target sequence is then allowed to hybridize both with oligonucleotides which are fully complementary and have oligonucleotides containing a mismatch, under conditions which will distinguish between the two. By manipulating the reaction conditions, it is possible to obtain hybridization only where there is full complementarity. If a mismatch is present there is significantly reduced hybridization.

The polymerase chain reaction (PCR) and reverse transcriptase PCR are techniques that amplify specific nucleic acid sequences with remarkable efficiency. Repeated cycles of denaturation, primer annealing and extension carried out with polymerase; e.g., a heat stable enzyme Taq polymerase, leads to exponential increases in the concentration of desired nucleic acid sequences. Given a knowledge of the nucleotide sequence of H-Ast 2, synthetic oligonucleotides can be prepared which are complementary to sequences which flank the nucleic acid of interest. Each oligonucleotide is complementary to one of the two strands. The nucleic acid can be denatured at high temperatures (e.g., 95° C.) and then reannealed in the presence of a large molar excess of oligonucleotides. The oligonucleotides, oriented with their 3' ends pointing towards each other, hybridize to opposite strands of the target sequence and prime enzymatic extension along the nucleic acid template. The end product is then denatured again for another cycle. After this three-step cycle has been repeated several times, amplification of a nucleic acid segment by more than one million-fold can be achieved. The resulting nucleic acid may then be directly sequenced.

In yet another method, PCR may be followed by restriction endonuclease digestion with subsequent analysis of the resultant products. Nucleotide substitutions can result in the gain or loss of specific restriction endonuclease sites. The gain or loss of a restriction endonuclease recognition site facilitates the detection of the organism using restriction fragment length polymorphism (RFLP) analysis or by detection of the presence or absence of a polymorphic restriction endonuclease site in a PCR product that spans the sequence of interest.

For RFLP analysis, nucleic acid is obtained, for example from the blood, gastric specimen, saliva, dental plaque, other bodily fluids of the subject suspected of containing H-Ast 2, is digested with a restriction endonuclease, and subsequently separated on the basis of size by agarose gel electrophoresis. The Southern blot technique can then be used to detect, by hybridization with labeled probes, the products of endonuclease digestion. The patterns obtained from the Southern blot can then be compared. Using such an approach, H-Ast 2 nucleic acid is detected and their mobility on the gel by determining the number of bands detected and comparing this pattern to the nucleic acid from H-Ast 2.

Similar creation of additional restriction sites by nucleotide substitutions at the disclosed mutation sites can be readily calculated by reference to the genetic code and a list of nucleotide sequences recognized by restriction endonucleases.

Single strand conformational analysis (SSCA) offers a relatively quick method of detecting sequence changes which may be appropriate in at least some instances.

In general, primers for PCR and LCR are usually about 20 bp in length and the preferable range is from 15–25 bp. Better amplification is obtained when both primers are the same length and with roughly the same nucleotide composition. Denaturation of strands usually takes place at 94° C. and extension from the primers is usually at 72° C. The annealing temperature varies according to the sequence under investigation. Examples of reaction times are: 20 mins denaturing; 35 cycles of 2 min, 1 min, 1 min for annealing, extension and denaturation; and finally a 5 min extension step.

PCR amplification of specific alleles (PASA) is a rapid method of detecting single-base mutations or polymorphisms. PASA (also known as allele specific amplification) involves amplification with two oligonucleotide primers such that one is allele-specific. The desired allele is efficiently amplified, while the other allele(s) is poorly amplified because it mismatches with a base at or near the 3' end of the allele-specific primer. Thus, PASA or the related method of PAMSA may be used to specifically amplify the mutation sequences of the invention. Where such amplification is done on H-Ast 2 isolates or samples obtained from an individual, it can serve as a method of detecting the presence of H-Ast 2.

As mentioned above, a method known as ligase chain reaction (LCR) can be used to successfully detect a single-base substitution. LCR probes may be combined or multiplexed for simultaneously screening for multiple different mutations. Thus, LCR can be particularly useful where, as here, multiple mutations are predictive of the same disease.

The present invention is more particularly descibed in the following examples which are intended as illustrative only since numerous modifications and variations therein will be apparent to those skilled in the art.

EXAMPLES

Example 1: Subgenomic RNA

To first examine the mechanism of replication of astroviruses, we analyzed the synthesis of proteins and RNA during a single-cycle infection of cultured cells (Monroe, S. S. et al., *J. Virol.*, 65: 641–648 (1991)). We detected a previously unreported 90-kDa protein that, by virtue of its reactivity with hyperimmune rabbit serum, is presumed to be a capsid protein precursor. This 90-kDa precursor could be cleaved by trypsin in vitro, with the appearance of three smaller proteins (31 kDa, 29 kDa, and 20 kDa). A second observation of our in vitro studies was a previously unreported 2.8-kb RNA that is polyadenylated and that we presumed to be a subgenomic mRNA encoding the 90-kDa precursor polypeptide.

cDNA Cloning and RNA Blot Hybridization.

Cell-culture-adapted human astrovirus serotype 2 (H-Ast2) was obtained from Dr. John Kurtz (Oxford, England), was plaque purified three times before use, and was propagated in LLCMK2 cells (ATCC CCL7.1) as previously described (Monroe, S. S. et al.). Double-stranded cDNA was synthesized from the polyadenylated fraction of RNA isolated from astrovirus infected cells (cDNA Cloning Kit, Boehringer Mannheim Biochemicals,), and was cloned into the pBluescript II plasmid vector (Stratagene). Recombinant clones were screened for astrovirus specific inserts by hybridization of [$^{32}$P]-labelled RNA transcribed in vitro from individual cDNA clones to total cytoplasmic RNA isolated from uninfected and astrovirus-infected cells.

Total cytoplasmic RNA isolated from astrovirus infected cells at the indicated times post infection and unlabeled RNA transcribed in vitro from cDNA clone 16, were resolved in a 1.2% agarose gel, transferred to a nylon membrane, and probed with [$^{32}$P]-labelled RNA transcribed from cDNA clone 16. The RNA transcripts from the insert in one cDNA clone (number 16) hybridized to both the 7.2- and 2.8-kb viral RNAs as evidenced by autoradiography of RNA blot hybridization (not shown). The hybridization reactivity was first detectable at 12 hours postinfection, coincident with detection of these RNAs by metabolic labeling (Monroe, S. S. et al.). The hybridization of a cRNA probe to both viral specific RNAs confirmed that the 2.8-kb RNA contains sequences present in the larger species, with the relative intensities indicating that the smaller RNA is present in at least a 10-fold molar excess. These observations support our earlier conclusion that the 2.8-kb RNA is a subgenomic mRNA (Monroe, S. S. et al.).

Nucleotide Sequence Analysis.

Sequence information for the subgenomic RNA was obtained by three approaches: 1) sequencing of supercoiled DNA from two plasmids with cDNA inserts, 2) sequencing of RNA purified from virions, and 3) amplification of genomic RNA by reverse transcriptase-polymerase chain reaction (RT-PCR), followed by sequencing of the double-stranded DNA products. Plasmid DNA and PCR products were sequenced using modified T7 DNA polymerase (Sequenase2®, US Biochemicals). Sequence information from the 5' end of the original clone was used to generate oligonucleotide primers for a second round of cDNA cloning from cytoplasmic RNA. PCR products were purified by gel filtration (Miniprep Spun Column, Pharmacia) before sequencing. RNA was sequenced using reverse transcriptase and dideoxynucleotide terminators (RNA Sequencing Kit, Boehringer Mannheim Biochemicals) with primers derived from the sequence of the cDNA clones. Although direct RNA sequencing often resulted in regions of the gels that were difficult to interpret, ambiguities were resolved through the use of RT-PCR sequencing over the same regions. The information from the three independent sequencing strategies was combined to arrive at a consensus sequence for the entire subgenomic region (Devereux, J. P. et al., *Nucleic Acids Res.*, 12: 387–395 (1984). The sequence derived from cDNA clone 16 contains a 19-nucleotide poly(A) tract immediately adjacent to the cloning linker, indicating that this cDNA insert is probably derived from the extreme 3' end of viral RNA. The location of the 5' end of the subgenomic RNA was estimated by primer runoff using total cytoplasmic RNA as template.

The consensus sequence for the unique region of the subgenomic RNA is 2484 nucleotides long and includes the following features: 1) an 11-nucleotide 5'-untranslated region (5'-UTR); 2) a 2388-nucleotide open reading frame (ORF); and 3) an 85-nucleotide 3'-UTR as set forth in SEQ ID NO: 3 and deposited with GenBank Data Library as Accession Number L06802.

Analysis of the Predicted Capsid Precursor Polypeptide.

The single ORF in the subgenomic RNA encodes a 796-amino-acid polypeptide with a predicted molecular mass of 88 kDa, consistent with the estimated 90-kDa mass of the capsid protein precursor we observed in infected cells (Monroe, S. S. et al.). At the amino terminus, the predicted polypeptide has a region of basic amino acids that may play a role as a nucleic acid binding motif. At the carboxy terminus is a region of acidic amino acids.

Comparison of the H-Ast2 Subgenomic RNA and Deduced Protein Sequences to the H-Ast1 Partial Sequence.

A comparison of the H-Ast2 RNA and deduced protein sequences to the partial sequences previously reported for H-Ast1 (Matsui, S. M. et al; Willcocks, M. M. et al., *Program Abstr. Third International Symposium*, Clearwater, Fla., abstr, pp. 2–47 (1992)) indicated regions of both similarities and differences. The nucleotide sequence immediately adjacent to the poly(A) tract, including the 3' UTR and the last 8 codons of the predicted ORF is 94% conserved, with only five differences and two single base insertions in the first 109 unique nucleotides. Four of the five differences, including two in the coding region, result in compensating changes that maintain base pairing in predicted stem-loop structures at the 3' ends of the RNAs.

Referring to FIG. 3. Predicted secondary structure at the 3' end of astrovirus RNA sequences. The structures were calculated by the method of Zuker and Stiegler (Needleman, S. B. et al., *J. Mol. Biol.*, 48: 443–453 (1970); Zuker, M. et al., *Nucleic Acids Res.*, 9: 133–148 (1981). The H-Ast1 structure contains a total of 154 nucleotides including 134 bases from the reported 3'-end sequence (Willcocks, M. M. et al. (1992)) plus 20 additional adenine residues. The H-Ast 2 structure contains 156 nucleotides corresponding to bases 2349 to 2504 in SEQ ID NO: 3. The region of the poly(A) tract involved in stem I is outlined with a box. The two insertions in the loop between stems I and II are shown with arrowheads. The residues within the conserved stem II that vary between the two serotypes are indicated. The terminator codons, in the loop of stem II, are marked with asterisks.

Note that stem I includes base pairs involving the poly(A) tract. The two insertions in the H-Ast2 sequence occur in a predicted loop between conserved stems I and II. The terminator UAG codons are located in the loop at the top of stem II, between the conservative changes. The stems marked III, although similar in predicted secondary structure, are composed of dissimilar sequences. The conserved primary and secondary structure at the 3' end of the genome may function as a recognition site during RNA replication. As a further indication that the primary sequence information in this 3' region is conserved among astroviruses, we have used oligonucleotide primers derived from this region to amplify RNA from all five reference serotypes of human astrovirus.

In contrast to the high degree of primary sequence conservation at the 3' end of the genome, there is only 59% nucleotide sequence identity in the consensus coding region sequence from H-Ast1 (Matsui S. M. et at (1993); Willcocks, M. M. et al., *Arch. Virol.*, 124: 279–289 (1992)) and the corresponding region of H-Ast2. Alignment of the 392 amino acid partial H-Ast1 sequence with the corresponding region of the H-Ast2 amino acid sequence indicates an overall similarity of 67%, with 52% identical residues. The proteins are more conserved at their carboxy termini, which both include the highly acidic region, with 80% similarity and 62% identity over the terminal 114 residues.

Example 2: Genomic RNA

H-Ast2 was propagated in vitro, and virion RNA was extracted and used as template for cDNA synthesis and sequence determination.

Human astrovirus was obtained from Dr. John Kurtz (Oxford, England) and propagated in LLCMK2 cells in Earle minimal essential medium (EMEM) supplemented with 5 µg of trypsin per ml as described (Herring; A. J. et al. (1981); Monroe, S. S. et al. (1991); Matsui et al. (1993)). Virions were partially purified from infected cell lysates by centrifuging through a 30% (w/v) sucrose cushion, suspended in TNE buffer containing 1% SDS, and extracted with phenol/chloroform. Virion RNA was precipitated with 2M LiCl and used for both the sequencing and the polymerase chain reaction (PCR) assays. Single-stranded cDNA was synthesized from virion RNA with super reverse transcriptase (Molecular Genetics Resources, Tampa, Fla.) using primers derived originally from cDNA sequence and subsequently from sequences determined by directly sequencing virion RNA, using a "primer walking" technique. DNA fragments of varying length were amplified by the PCR assay with Taq polymerase (Perkin-Elmer Co., Norwalk, Conn.) and virus-specific primers. Sequences were determined from three sources: virion RNA, PCR DNA, and cDNA clones. Virion RNA was directly sequenced by using an RNA sequencing kit (Boehringer Mannheim, Indianapolis, Ind.). Both the PCR DNA and the cloned cDNA were purified by using miniprep spun columns (Pharmacia, Piscataway, N.J.) and sequenced by using the Sequenase Version 2.0 DNA Sequencing Kit (USB, Cleveland, Ohio). Sequences on both strands of DNA were determined with each base sequenced an average of at least four times. Sequences were assembled and aligned by using the Genetics Computer Group (GCG) sequence analysis program (Devereux et al, *Nucleic Acids Res.*, 12: 387 (1984)) and a consensus sequence was derived. Sequences of the 5' and 3' ends of the genomic RNA were determined by following the procedure of Lambden et al., (*J. Virol.*, 66: 1817 (1992)). Briefly, a synthetic primer 1 was ligated to the 3' ends of virion RNA or cDNA corresponding to the 5' end of virion RNA with T4 RNA ligase (GIBCO BRL, Gaithersburg, Md.). cDNA fragments (400- to 600-bp) spanning either the 5' or the 3' ends were produced by the PCR amplification using a primer 2 complementary to the primer 1 and virus-specific primers, and sequenced by using internal primers.

The genomic RNA of H-Ast2 is 6,797 nucleotides in length, excluding 31 adenines (poly A tail) at the 3' end as set forth in SEQ ID NO: 1 and deposited with GenBank Data Library as accession number L13745. The genome possesses three overlapping open reading frames (ORFs) designated 1a, 1b, and 2 and depicted in FIG. 2.

Figure 1:
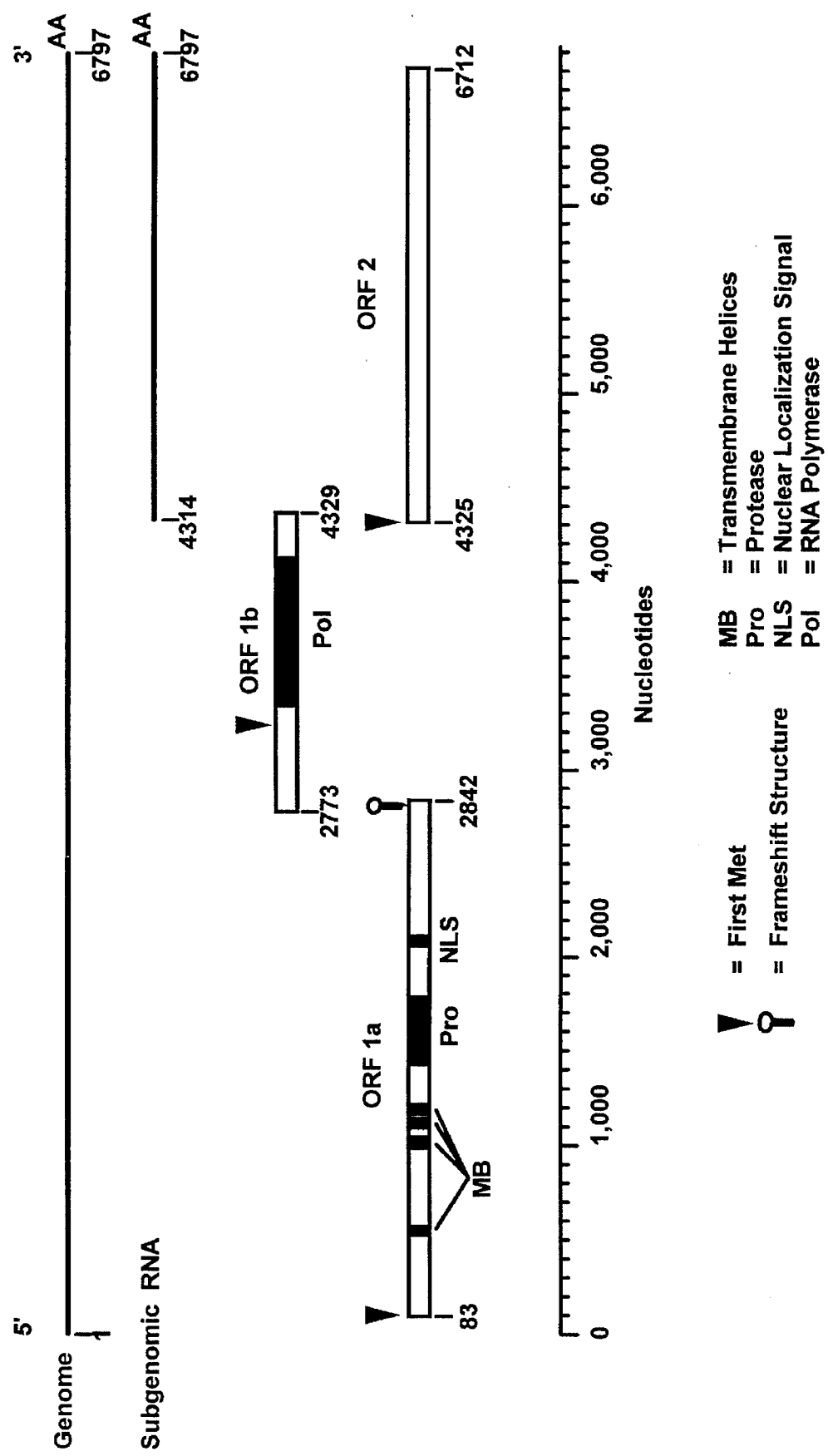
FIG. 1 shows the genomic organization of human astrovirus. The locations of three ORFs, the first methionine (Met), and the frameshift site are indicated. The predicted transmembrane helices (MB), protease (Pro), nuclear localization signal (NLS), and RNA-dependent RNA polymerase (Pol) are indicated by stippled boxes.

Referring to FIG. 1, the sequences surrounding the first AUG codons of ORFs 1a and 2 are predicted to be optimal for the initiation of translation (Kozak, M. et al., *J. Biol. Chem.*, 266: 19867 (1991). ORF 1a is preceded by 82 untranslated nucleotides and encodes a polypeptide of 920 amino acids. The 5' untranslated region of the genomic RNA was analyzed using the RNAFOLD program (Zuker, M. et al. (1981)). This region was predicted to contain extensive secondary structure, as demonstrated by the characteristic stem-loop structures preceding the initiation AUG codon.

ORF 1b,which overlaps ORF1a by 70 nucleotides, is in reading frame +1 and its first AUG codon, which is predicted to be weak, is located 380 nucleotides downstream of the ORF 1atermination codon. ORF 2, present also in the subgenomic RNA, overlaps ORF 1b by 5 nucleotides, begins with a start codon at nucleotide 4325, and ends with a stop codon 82 bases from the 3' end. As we recently reported, ORF 2 codes for a capsid protein precursor of 796 amino acids with a predicted molecular mass of 88 kDa.

The existence of two separate ORFs (1a and 1b) located in two different reading frames prompted us to examine the 70-nucleotide overlap region in greater detail. A ribosomal frameshift signal was identified, consisting of the "shifty" heptanucleotide (AAAAAAC) from position 2,791 to 2,797, followed by a stem-loop structure that may form a pseudoknot with a downstream sequence. The putative frameshift signal of the astrovirus showed resemblance to those at the gag-pro junction of some retroviruses, such as mouse mammary tumor virus (MMTV) (FIG. 2B), and fit the simultaneous tRNA slippage model of −1 frameshifting described for the synthesis of the gag-related polyproteins (Jacks, Et. et al., *Cell*, 55: 447 (1988)). Ribosomal frameshifting recently has been shown to be a normal expression mechanism in several groups of positive-strand RNA viruses, namely animal coronaviruses and arteriviruses, and plant luteoviruses and dianthoviruses (Briefly, I. et al., *Cell*, 57: 537 (1989); den Boon, J. et al., *J. Virol.*, (1991); Prufer, D. et al., *EMBO J.*, 11: 1111 (1992)). However, the putative frameshifting signal of astrovirus was much less similar to the frameshift regions of these viruses than to those of some retroviruses (not shown). The ribosomal frameshifting during translation of astrovirus RNA directs the synthesis of an ORF 1a/1b fusion nonstructural polyprotein of 1,416 amino acids with a predicted molecular mass of 161 kDa as set forth in SEQ ID NO: 4. The predicted transmembrane α-helices occur at residues 156–172, 308–333, 343–362, and 369–387, the predicted cleavage site at the N-terminus of the putative VPg-protease occur at residues 419–420, the putative nuclear localization signal occur at residues 666–682, and the fusion dipeptide (KK) occur at residues 904–905.

The nucleotide sequence of the astrovirus genomic RNA and the deduced amino acid sequences of the nonstructural polyprotein and the capsid protein were compared with the current sequence databases (Altschulet al., *J. Mol. Biol.*, 215: 403 (1990); Henikoff, S. et al., *Proc. Natl. Acad. Sci. USA*, 89: (1992)). Apart from the obvious similarity to several partial H-Ast1 sequences (Monroe, S. S. et al., (1991); Matsui, S. M. et al., (1993); Willcocks, M. M. et al. (1992); Jiang, B. et al., unpublished), statistically significant sequence similarity was observed between a region in the C-terminal portion of the nonstructural polyprotein and the putative RNA-dependent RNA polymerases (RdRps) of plant bymoviruses and potyviruses (score of 75 corresponding to the Poisson probability of random matching (P) of 0.015 was observed with the putative RdRp of barley yellow mosaic bymovirus, and score of 73 (P=0.095) was found with Ornithogalum mosaic potyvirus RdRp). Further analysis using the previously published multiple alignment revealed in the putative astrovirus polymerase the eight conserved motifs typical of the positive-strand RNA virus RdRps and showed that it belongs to the so-called supergroup I, which includes the polymerases of picornaviruses, caliciviruses, potyviruses, and several other groups of plant viruses (Koonin, E. V. et al., *J. Gen. Virol.*, 72: 2197 (1991); Dolja, V. V. et al., *Semin. Virol.*, 3: 315 (1992); Koonin, E. V. et al., *Crit. Rev. Biochem. Mol. Biol.*, in press).

A more sensitive analysis performed by comparing the astrovirus protein sequences with a database of positive-strand RNA virus sequences showed a region of the similarity between the polyproteins of H-Ast2 and rabbit hemorrhagic disease virus (RHDV). This region included the putative catalytic cysteine of the RHDV protease. Using the previously published alignments of chymotrypsin-related proteases of positive-strand RNA viruses, we identified, in the putative protease domain of astrovirus, the conserved segments surrounding the three catalytic amino acid residues and a fourth distal segment implicated in substrate binding (Gorbalenya, A. E. et al., *FEBS Lett.*, 243: 103 (1989)). A triple alignment of moderate statistical significance could be generated for the putative proteases of H-Ast2 and two calicviruses (Gorbalenya, A. E. et al. (1989)).

An important feature of the putative protease of H-Ast2 is the substitution of serine for the catalytic cysteine found in the majority of positive-strand RNA virus proteases of superfamily I. Previously, an analogous substitution has been found in the putative proteases of sobemoviruses, luteoviruses and arteriviruses (Gorbalenya, A. E. et al. (1989 and 1988); Bazan, J. F. et al., (1989 and 1990); den Boon, J. A. et at. (1991)). However, the putative protease of H-Ast2 showed lower similarity to these viral proteases than to the cysteine proteases of caliciviruses.

An extensive search of the astrovirus nonstructural polyprotein sequence for the motifs defining other conserved domains of positive-strand RNA viruses, namely RNA helicase, methyltransferase, and papain-like protease (Gorbalenya, A. E. et al., *Nucleic Acids Res.*, 17: 4713 (1989); Gorbalenya, A. E. et al., *FEBS Lett.*, 152: 145 (1990); Gorbalenya, A. E. et al., *FEBS Lett.*, 188: 201 (1991); Rozanov, M. N. et al., *J. Gen. Virol.*, 73: 2129 (1992)), failed to identify any candidate regions. The absence of the helicase domain is remarkable as so far this domain has been identified in all positive-strand RNA viruses with genomes larger than 6,000 nucleotides (Gorbalenya, A. E. et al., *Nucleic Acids Res.*, 17: 8413 (1989)). The absence of the methyltransferase domain suggested that the astrovirus encodes VPg, a protein covalently linked to the 5' end of the vital genome (Wimmer, E. et al., *Cell*, 28: 199 (1982); Vartapetian, A. B. et al., *Prog. Nucl. Acids Res. Molec. Biol.*, 34: 209 (1987)), compatible with the affinity of the putative H-Ast2 polymerase with supergroup I RdRps, which mostly belong to VPg-containing viruses (Koonin, E. V. et al. (1991); Dolja, V. V. et al (1992); Koonin, E. V. et al. in press)).

Additional features detected by analysis of the nonstructural polyprotein of H-Ast2 included four transmembrane α-helices and a nuclear localization signal (FIG. 1). The transmembrane helices were located in the region upstream of the protease and they may be involved in membrane anchoring of the viral RNA replication complex, as described for the 3A or 3AB proteins of poliovirus (Giachetti, C. et.al., *J. Virol.*, 65: 2647 (1991); Giachetti, C. et al., *J. Virol.*, 66: 6046 (1992). In all positive-strand RNA viruses for which the location of the VPg domain in the polyprotein is known, the domain is found within a short region between a (putative) transmembrane segment and the protease (Koonin, E V., unpublished observations). VPg is linked to the 5' end of the viral RNA via a tyrosine or a serine residue (Wimmer, E. (1982); Vartapetian, A. B. et al. (1987) ). Inspection of the respective region of the H-Ast2 polyprotein revealed no appropriately located tyrosines and only one serine (Ser 420). It is tempting to speculate that this serine may be the RNA-linking amino acid of VPg. Moreover, as it is preceded by a glutamine residue, thus forming a canonical cleavage site for the viral protease, it is possible that the active serine is located at the very N-terminus of the astrovirus VPg, similar to the VPg of comoviruses (Hellen, C. U. T. et al., *Biochemistry*, 28: 9881 (1990); Palmenberg, A. et al.*A. Rev. Microbiol.*, 44: 603 (1990); Eggen, R. et al., in RNA Genetics, P. Ahlquist, J. et al., eds., *Vol.*, 1 p. 49, CRC Press, Boca Raton (1988); Chen, X. et al., *Virology*, 191: 607 (1992)). The nuclear localization signal (NLS), spanfling amino acids 666 to 682, is identical to that of H-Ast1 (Willcocks, M. M. et al., (1992)). This signal may be involved in transport of astrovirus proteins to the nucleus, as substantiated by the observation that astrovirus products were detected by immunofluorescence in the nucleus of bovine astrovirus-infected cells (Aroonprasert, D. et al., *Vet. Microbiol.*, 19: 113 (1989)). The astrovirus NLS perfectly fits the consensus for the bipartite signal motif comprising two clusters of basic amino acid residues separated by a ten-residue spacer region (Dingwall, C. et al., *Trends Biochem. Sci.*, 16: 478 (1991)). In a curious analogy, both the protease and the RdRp of potyviruses contain similar NLS and are accumulated in the nuclei of infected plant cells (Carrington, J. C. et al., *Plant Cell*, 3: 953 (1991); Li, X. H. et al., *Virology*, 193: 951 (1993)).

Screening failed to detect other sequences significantly similar to the capsid protein of H-Ast2, direct comparison of this capsid sequence with the sequences of other positive-strand RNA virus capsid proteins identified a conserved domain with hepatitis E virus (HEV), an agent phylogenetically remote from astrovirus and other supergroup I viruses in terms of the comparison of RdRps and the other principal nonstructural domains (Koonin, E. V. et al., *Proc. Natl. Acad. Sci. USA*, 89: 8259 (1992)). Since both astrovirus and HEV replicate in the human gut, this consented domain might have resulted from a recombinational event during coinfection. Of interest, astrovirus has previously been reported in association with fatal hepatitis in ducklings, suggesting a possible hepatic tropism for this virus (Gough, R. E. et al., *Vet. Rec.*, 114: 279 (1984)).

To gain further insight into the evolutionary relationship of astroviruses, we generated a tentative phylogenetic tree (Felsenstein, J. et al., *Cladistics*, 5: 164 (1989)) for the supergroup I RdRps, including the H-Ast2 sequence. The result showed that astroviruses constitute a distinct evolutionary lineage not closely associated with any other group of viruses.

Our data show that astroviruses have no close relatives among other viruses, as demonstrated by comparative sequence analysis, and that their genomic organization is novel among animal viruses. It is remarkable, however, that astroviruses combine features typical of several very different groups of positive-strand RNA viruses and even retroviruses (the frameshift signal). Of special interest is the similarity of the genomic organization and expression strategy of astrovirus and plant luteoviruses (Martin, R. R. ct al., *Annu. Rev. Phytopathol.*, 28: 341 (1990)). Both groups of viruses lack the helicase domain, while the protease and the polymerase domains arc apparently fused via ribosome frameshifting. Moreover, this analogy correlates with the substitution of serine for the catalytic cysteine in the viral proteases.

The present findings strongly support the classification of astroviruses in a new family, Astroviridae. The availability of sequence information will be useful in the development of sensitive new diagnostic assays to further our understanding of the importance of this group of viruses as a cause of disease in humans and animals.

Throughout this application, various publications are referenced. The disclosures of these publications in their entireties are hereby incorporated by reference into this application in order to more fully describe the state of the art to which this invention pertains.

Although the present process has been described with reference to specific details of certain embodiments thereof, it is not intended that such details should be regarded as limitations upon the scope of the invention except as and to the extent that they are included in the accompanying claims.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 6828 base pairs
( B ) TYPE: nucleic acid
( C ) STRANDEDNESS: single
( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
( A ) ORGANISM: Human Astrovirus
( B ) STRAIN: Serotype 2

( v i i i ) POSITION IN GENOME:
( C ) UNITS: 100%

( x i ) SEQUENCE DESCRIPTION: SEQ ID NO:1:

```
CCAAGAGGGG GGUGGUGAUU GGCCUUUGGC UUAUCAGUGU GUAUAUAAGA UUUCUACACU      60
CUUUUAUCAA GUACUCUACA GGAUGGCACA CGGUGAGCCA UACUACAGUU CUAAACCUGA     120
CAAAGAUUUC AAUUUUGGAA GCACAAUGGC ACGUAGGCAA AUGACACCUA CCAUGGUUAC     180
AAAGCUUCCC AAGUUUGUUA GGAAUUCUCC ACAAGCCAUU GAUUGGAUCG UAAGAGGUCU     240
AAUCUUCCCC ACCACUGGAA AAACUUAUUU CCAACGAGUU GUUGUGAUUA CCGGUGGGCU     300
UGAGGAUGGA ACAUAUGGCU CAUUCGCAUU UGAUGGUAGA GAAUGGGUAG AGAUCUACCC     360
AAUAGAGCAU CUAAAUCUCA UGUCAUCUUU GAAACUAAUA CACAAAGCCA AUGCUCUUCA     420
GGAGAGAUUA CGUCUCUCCC AAGAAGAGAA AGCCACCCUU GCUCUUGAUG UGCAAUUCCU     480
UCAGCAUGAA AACGUGCGAC UGAAGGAAUU GAUUCCAAAA CCAGAGCCAC GGAAGAUACA     540
GAUGAAGUGG AUAAUUGUAG GAGCAGUGCU UACAUUUUUA UCUCUAAUAC CUGGGGCUA     600
UGCGCAAAGU CAGACCAACA ACACUAUAUU UACAGAUGUG AUAGCUGCCU GCAAAUAUUC     660
AACUGAGACA UUAACAGAAA ACCUUGACCU UAGAAUCAAG CUCGCACUAG CAAACAUAAC     720
CAUUAGUGAC AAGUUAGACG CUGUGAGGCA AAUUCUUAAC UUUGCCUUUG UACCUAGAGC     780
UCAUUGGUUG AGAACUGUUU UCUACUACAU CCAUUAUUAU GAAAUGUGGA AUAUUUUUAU     840
GUUUGUUCUU GCAAUUGGCA CUGUCAUGAG GAGCGCCCGC CCCGGUACAG ACUUAAUCAC     900
ACUUGCAACG UCCCACUUGU CUGGUUUUAG GCUGGCUGUU UUACCCACAA UUCCAUUCCA     960
UACCACUAUG ACUUUGUGGG UCAUGAACAC UCUUAUGGUU UGUUACUAUU UUGAUAAUUU    1020
GCUAGCAAUA ACAAUGGCAA UCUUAGCACC AAUCCUUGGC AUCAUCUUCU UGUGCUUCAU    1080
GGAAGACUCC AAUUAUGUGA GCCAGAUACG UGGUCUUAUU GCCACAGCAA UAUUAAUUGC    1140
```

-continued

| | | | | | | |
|---|---|---|---|---|---|---|
| UGGUGGGCAU | GCCUGUUUGA | CACUCACAGG | CACAACCACG | UCAUUAUUUG | CUGUCAUACU | 1200 |
| AACUUGUAGG | UUCAUACGUA | UGGCGACGGU | UUUUAUUGGC | ACCAGAUUCG | AGAUCCGUGA | 1260 |
| UGCUAAUGGG | AAGGUCGUGG | CUACUGUACC | AACUAGGAUC | AAAAAUGUUG | CAUUUGACUU | 1320 |
| CUUCCAGAAG | CUAAACAGU | CAGGGGUGAG | AGUUGGAGUC | AACGAAUUCG | UUGUUAUAAA | 1380 |
| ACCAGGUGCA | UUAUGUGUCA | UAGACACCCC | UGAAGGGAAA | GGAACAGGUU | UCUUUUCUGG | 1440 |
| CAAUGACAUA | GUAACAGCAG | CACAUGUUGU | UGGCAAUAAU | ACUUUGUGA | AUGUGUGCUA | 1500 |
| CGAGGGCUUG | AUGUACGAAG | CGAAAGUUCG | UUACAUGCCU | GAAAAGGACA | UAGCAUUCAU | 1560 |
| AACUUGUCCU | GGUGACUUGC | AUCCAACAGC | AAGAUUAAAA | UUAUCAAAGA | ACCCAGAUUA | 1620 |
| UAGUUAUGUC | ACAGUCAUGG | CUUACGUGAA | UGAAGAUCUU | GUGGUUUCAA | CCGCAGCUGC | 1680 |
| CAUGGUGCAU | GGUAACACUC | UCUCAUAUGC | AGUUCGCACC | CAAGACGGGA | UGUCGGGUGC | 1740 |
| ACCAGUUUGU | GACAAGUAUG | GUCGGGUGUU | GGCAGUCCAU | CAAACCAAUA | CUGGGUACAC | 1800 |
| UGGAGGUGCU | GUCAUAAUAG | ACCCAGCAGA | CUUUCAUCCA | GUGAAGGCCC | CAUCUCAGGU | 1860 |
| GGAAUUGCUC | AAAGAGGAAA | UAGAGCGACU | AAAAGCCCAA | UUGAAUUCCG | CCGCUGAGAA | 1920 |
| CCCAGCGACU | GUUGCUACAC | AACAACCUGC | CAUUACAUUA | GAACAGAAAA | GUGUUAGCGA | 1980 |
| CAGUGAUGUU | GUUGACCUUG | UCAGAACUGC | AAUGGAACGU | GAGAUGAAGG | UACUGCGUGA | 2040 |
| UGAAAUCAAU | GGGAUACUUG | CACCAUUUCU | ACAAAAAAG | AAAGGUAAGA | CCAAGCAUGG | 2100 |
| UAGGGGUAGA | GUCAGACGUA | ACCUUAGAAA | AGGCGUGAAA | CUCCUUACUG | AGGAAGAGUA | 2160 |
| UCGAGAACUC | UUAGAGAAAG | GUCUAGAUCG | UGAGACAUUC | CUUGACCUUA | UAGACCGCAU | 2220 |
| UAUUGGAGAG | AGGUCUGGCU | ACCCUGACUA | UGAUGAUGAG | GAUUAUUAUG | AUGAAGAUGA | 2280 |
| UGAUGGAUGG | GGAAUGGUUG | GUGAUGAUGU | AGAAUUUGAU | UAUACUGAAG | UAAUUAAUUU | 2340 |
| UGACCAAGCA | AAACCAACUC | CUGCCCCAAG | AACAACCAAG | CCAAAACCUU | GCCCCGAGCC | 2400 |
| AGAAACUGAA | ACACAACCAC | UUGAUUUGUC | UCAGAAGAAA | GAGAAACAAC | CAGAACAUGA | 2460 |
| ACAACAAGUG | GUGAAGUCUA | CCAAGCCUCA | GAAGAAUGAA | CCUCAGCCAU | AUUCACAAAC | 2520 |
| UUAUGGCAAG | GCACCAAUCU | GGGAAUCUUA | UGAUUUUGAC | UGGGACGAGG | AUGAUGCCAA | 2580 |
| GUUCAUCCUG | CCAGCACCAC | ACCGGUUAAC | UAAGGCAGAU | GAAAUAGUUC | UUGGGUCAAA | 2640 |
| AAUUGUCAAG | CUUAGGACGA | UUAUUGAAAC | AGCCAUUAAG | ACCCAGAACU | AUAGUGCACU | 2700 |
| ACCUGAAGCU | GUGUUUGAGC | UCGACAAAGC | AGCUUAUGAA | GCAGGUCUAG | AAGGUUUCCU | 2760 |
| CCAAAGAGUU | AAAUCGAAAA | ACAAGGCCCC | AAAAAACUAC | AAAGGGCCCC | AGAAGACCAA | 2820 |
| GGGGCCCAAA | AUUAUCACUC | AUUAGAUGCA | UGGAAAUCAU | UGCUAGAACC | UCCACGUGAG | 2880 |
| CGGAGGUGCG | UACCUGCUAA | UUUUCCAUUG | UUAGGUCAUU | UACCAAUUAA | UAGACCCAUC | 2940 |
| UUUGAUGAUA | AGAAACCCAG | GGAUGAUCUC | CUUGGAUUAC | UUCCAGAACC | AACCUGGCAU | 3000 |
| GCUUUUGAGG | AAUAUGGACC | AACUACAUGG | GGCCCACAAG | CUUUCAUUAA | GUCUUUUGAU | 3060 |
| AAAUUCUUUU | AUGCAGAACC | AAUUGAUUUU | UUUCAGAAU | AUCCACAGUU | GUGUGCUUUC | 3120 |
| GCUGAUUGGG | CAACUUAUCG | CGAGUUUCGG | UAUCUAGAGG | ACACUAGAGU | GAUACACAUA | 3180 |
| ACUGCAACUG | AGAAGAAUAC | UGAUUCAACA | CCUGCAUAUC | CUAAAAUGAA | UUAUUUUGAU | 3240 |
| ACUGAAGAAA | GUUAUUUGGA | AGCACAUGGG | UGGGCUCCAU | AUAUUAGAGA | AUUCACUAGG | 3300 |
| GUCUUCAAAG | GAGACAAACC | UGAAGUACUG | UGGUACCUAU | UCUUAAGAA | AGAGAUCAUU | 3360 |
| AAGGAGGAAA | AAGUUAAAAA | UUCUGAUAUC | CGGCAGAUAG | UAUGUGCCGA | UCCCAUUUAC | 3420 |
| ACCAGGAUAG | GGGCGUGCUU | AGAGGCACAU | CAGAAUGCUU | UGAUGAAACA | GCAUACCGAU | 3480 |
| ACUUCAGUUG | GUCAGUGUGG | GUGGUCACCA | AUGGAAGGCG | GCUUUAAAAA | AACAAUGCAA | 3540 |

```
CGCCUAGUAA AUAAAGGGAA UAAGUACUUU AUUGAAUUUG ACUGGACCCG CUAUGAUGGA    3600
ACUAUACCAC CAGCACUUUU CAAACACAUC AAAGAAAUUA GGUGGAAUUU CAUCAAUAAA    3660
GACCAACGUG AAAAGUACAG ACAUGUGCAU GACUGGUAUG UUGACAACCU CCUUAACCGC    3720
CAUGUACUUC UACCAUCUGG UGAAGUUACC UUGCAGACAC GAGGCAAUCC AUCGGGCAG     3780
UUUUCAACAA CAAUGGAUAA UAACAUGGUC AAUUUUGGC UACAAGCUUU UGAGUUCGCU     3840
UAUUUCAAUG GCCCAGACAA AGACCUUUGG AAGACCUAUG ACACUGUGGU UUAUGGAGAU    3900
GACAGGCUCU CUACAACACC UUCGGUACCU GAUGAUUAUG AGGAGAGAGU GAUCACUAUG    3960
UAUAGAGACA UCUUUGGCAU GUGGGUUAAG CCCGGAAGG UCAUCUGUAG AAACAGCAUA     4020
GUUGGAUUAU CCUUUUGUGG CUUUACUGUU AAUGAAAAUC UUGAACCUGU GCCAACCUCU    4080
CCGGAAAAGU UGAUGGCAUC ACUGCUAAAG CCUAUAAAG UUUUACCUGA UCUUGAAUCA     4140
CUCCAUGGGA AGCUCCUAUG CUAUCAGUUG CUUGCUGCGU UCAUGGCAGA AGAUCACCCU    4200
UUUAAGGUGU AUAUAGAACA CUGCCUAUCA CGGACUGCAA AGCAGCUUCG UGACUCUGGC    4260
CUACCGGCCA GGCUCACAGA AGAGCAACUC CAUCGCAUUU GGAGGGGAGG ACCAAAGAAG    4320
UGUGAUGGCU AGCAAGUCUG ACAAGCAAGU CACUGUUGAG GUCAAUAACA AUGGCCGAAA    4380
CAGGAGCAAA UCCAGAGCUC GAUCACAAUC UAGAGGUCGA GGUAGAUCAG UCAAAAUCAC    4440
AGUCAAUUCU CACAACAAAG GCAGAAGACA AAACGGACGC AACAAAUAUC AAUCUAAUCA    4500
GCGUGUCCGU AAAAUUGUCA AUAAACAACU CAGGAAACAG GGUGUCACAG GACCAAAACC    4560
UGCAAUAUGC CAGAGAGCCA CAGCAACACU GGGACAAUU GGAUCAAACA CAACAGGAGC     4620
AACAGAGAUC GAGGCGUGCA UACUCCUUAA UCCCGUCCUG GUUAAGGACG CUACUGGAAG    4680
UACUCAGUUU GGGCCAGUGC AGGCGCUAGG UGCUCAGUAU UCAAUGUGGA AACUAAAGUA    4740
UUUGAAUGUU AAACUGACUU CCAUGGUGGG CGCCUCAGCU GUUAACGGGA CUGUACUCCG    4800
CAUCUCGCUC AACCCUACAU CCACUCCAUC AUCAACUAGC UGGUCUGGAC UUGGUGCUCG    4860
UAAGCACAUG GAUGUUACAG UGGGCAGGAA UGCAGUCUUU AAACUUAGAC CAUCAGACCU    4920
UGGAGGGCCA AGGGAUGGCU GGUGGCUCAC UAAUACCAAU GACAAUGCAU CUGAUACAUU    4980
AGGCCCAUCU AUUGAAAUUC ACACCCUUGG UAAAACCAUG UCUUCAUAUA AAAAUGAGCA    5040
AUUUACAGGU GGACUAUUUC UUGUUGAGCU UGCUUCAGAA UGGUGUUUUA CUGGCUAUGC    5100
AGCUAAUCCA AAUUUAGUUA AUUUGGUUAA AUCCACUGAU CAUGAGGUGA AUGUCACUUU    5160
UGAGGGCUCA AAAGGUACGC CCCUAAUAAU GAAUGUCGCA GAGCACAGCC ACUUUGCAAG    5220
AAUGGCUGAA CAACAUUCCU CCAUCUCAAC AACAUUUUCA AGAGCUGGAG GCGAUGCAAC    5280
AUCUGACACU GUUUGGCAGG UGCUGAACAC AGCAGUCUCA GCAGCAGAGC UUGUAGCCCC    5340
ACCACCGUUC AAUUGGCUUA UAAAGGGUGG CUGGUGGUUU GUAAAGUUGA UUGCAGGUAG    5400
AACUAGAACU GGUACCAAGC AAUUUAUGU UUACCUAGU UAUCAGGAUG CUUUAUCAAA      5460
UAAACCAGCU CUUUGCACUG GUGGAGUUAC AGGUGGCGUU CUACGUACCA CACCGGUAAC    5520
AACUCUACAG UUCACUCAAA UGAACCAGCC AAGCCUUGGG CAUGGUGAGC ACACUGCCAC    5580
CAUUGGCAGU AUUGUGCAAG AUCCAAGUGG GGAACUGCGU GUGCUGCUAA CAGUUGGCUC    5640
AAUCAUGAGC CCGAAUUCAG CUGAUAGGCA AGUUUGGCUG AACAAAACUC UGACAGCGCC    5700
AGGAACAAAU UCAAUGACA AUCUUGUAAA GAUAGCCCAC GACUUGGGUC ACUAUUUGAU     5760
CAUGCAAGGG UUUAUGCAUA UAAAGACAGU AGAGUGGUAU ACUCCUGAUU UUCAACCUUC    5820
GCGUGACCCA ACCCCUAUUG CUGGCAUGUC AGUGAUGGUU AACAUAACAA AGAAGGCUGA    5880
UGUCUACUUC AUGAAGCAAU UCAAAAAUUC UUACACCAAC AACCGCCAUC AAAUAACAAG    5940
```

```
CAUCUUUUUA  AUUAAACCAU  UGGCAGAUUU  UAAGGUGCAA  UGUUAUAUGA  GCUACUUUAA    6000

AAGAGAGUCA  CAUGACAAUG  AUGGGGUUGC  CAAUCUUACA  GUGAGAAGUA  UGACCAGCCC    6060

GGAGACUAUC  AGGUUUCAAG  UUGGAGAAUG  GUAUUUGCUA  ACAAGUACCA  CACUUAAGGA    6120

GAACAACCUA  CCAGAGGGCU  GGGUUUGGGA  UAGGGUGGAG  CUUAAGAGUG  ACACACCAUA    6180

CUAUGCUGAU  CAAGCAUUGA  CAUAUUUCAU  AACACCACCC  CCAGUGGACU  CCCAAAUUUU    6240

AUUUGAAGGU  AACACCACAU  UGCCCAGAAU  UUCCUCUCCG  CCUGACAAUC  CAGCGGGCG     6300

AUAUAUGGAA  AGCCACCAGC  AAGACUGUGA  CUCUUCUGAU  GAUGAGGAU   AUUGUGAAAA    6360

UGUUUCAGAG  GAGACAGAAA  CUGAGGAUGA  GGAAGAUGAG  GACGAAGACG  AUGAAGCGGA    6420

CAGGUUUGAU  CUCCACAGCC  CCUAUAGUUC  UGAACCUGAG  GACUCUGAUG  AGAACAACCG    6480

UGUAACCCUC  CUCUCUACAC  UCAUAAACCA  AGGAAUGACA  GUGGAGCGCG  CAACAAGAAU    6540

AACUAAACGC  GCUUUCCCAA  CCUGCGCUGA  GAAACUGAAG  CGCAGCGUGU  ACAUGGACCU    6600

GCUUGCCUCC  GGUGCAUCGC  CGAGCAGUGC  AUGGUCAAAC  GCGUGUGAUG  AAGCACGCAA    6660

UGUGGGCAGC  AAUCAGCUGG  CCAAACUUUC  UGGAGACCGC  GGCCACGCCG  AGUAGGAUCG    6720

AGGGUACAGU  CUCCAUUACU  UUUCUGUCUC  UGUUUAGAUU  AUUUUAAUCA  CCAUUUAAAA    6780

UUGAUUUAAU  CAGAAGCAAA  AAAAAAAAA   AAAAAAAAA   AAAAAAA                   6828
```

(2) INFORMATION FOR SEQ ID NO:2:

(i) SEQUENCE CHARACTERISTICS:
  (A) LENGTH: 4247 base pairs
  (B) TYPE: nucleic acid
  (C) STRANDEDNESS: single
  (D) TOPOLOGY: linear (ii) MOLECULE TYPE: RNA (genomic)

(iii) HYPOTHETICAL: NO (iv) ANTI-SENSE: NO (vi) ORIGINAL SOURCE:
  (A) ORGANISM: Human Astrovirus
  (B) STRAIN: Serotype 2

(xi) SEQUENCE DESCRIPTION: SEQ ID NO:2:

```
AUGGCACACG  GUGAGCCAUA  CUACAGUUCU  AAACCUGACA  AAGAUUUCAA  UUUUGGAAGC    60

ACAAUGGCAC  GUAGGCAAAU  GACACCUACC  AUGGUUACAA  AGCUUCCCAA  GUUGUUAGG     120

AAUUCUCCAC  AAGCCUAUGA  UUGGAUCGUA  AGAGGUCUAA  UCUUCCCAC   CACUGGAAAA    180

ACUUAUUUCC  AACGAGUUGU  UGUGAUUACC  GGUGGGCUUG  AGGAUGGAAC  AUAUGGCUCA    240

UUCGCAUUUG  AUGGUAGAGA  AUGGGUAGAG  AUCUACCCAA  UAGAGCAUCU  AAAUCUCAUG    300

UCAUCUUUGA  AACUAAUACA  CAAAGCCAAU  GCUCUUCAGG  AGAGAUUACG  UCUCUCCCAA    360

GAAGAGAAAG  CCACCCUUGC  UCUUGAUGUG  CAAUUCCUUC  AGCAUGAAAA  CGUGCGACUG    420

AAGGAAUUGA  UUCCAAAACC  AGAGCCACGG  AAGAUACAGA  UGAAGUGGAU  AAUUGUAGGA    480

GCAGUGCUUA  CAUUUUAUC   UCUAAUACCU  GGGGGCUAUG  CGCAAAGUCA  GACCAACAAC    540

ACUAUAUUUA  CAGAUGUGAU  AGCUGCCUGC  AAAUAUUCAA  CUGAGACAUU  AACAGAAAAC    600

CUUGACCUUA  GAAUCAAGCU  CGCACUAGCA  ACAUAACCA   UUAGUGACAA  GUUAGACGCU    660

GUGAGGCAAA  UUCUUAACUU  UGCCUUUGUA  CCUAGAGCUC  AUUGGUUGAG  AACUGUUUUC    720

UACUACAUCC  AUUAUUAUGA  AAUGUGGAAU  AUUUUUAUGU  UGUUCUUGC   AAUUGGCACU    780

GUCAUGAGGA  GCGCCCGCCC  CGGUACAGAC  UUAAUCACAC  UUGCAACGUC  CCACUUGUCU    840
```

```
GGUUUUAGGC  UGGCUGUUUU  ACCCACAAUU  CCAUUCCAUA  CCACUAUGAC  UUUGUGGGUC   900

AUGAACACUC  UUAUGGUUUG  UUACUAUUUU  GAUAAUUUGC  UAGCAAUAAC  AAUGGCAAUC   960

UUAGCACCAA  UCCUUGGCAU  CAUCUUCUUG  UGCUUCAUGG  AAGACUCCAA  UUAUGUGAGC  1020

CAGAUACGUG  GUCUUAUUGC  CACAGCAAUA  UUAAUUGCUG  GUGGGCAUGC  CUGUUUGACA  1080

CUCACAGGCA  CAACCACGUC  AUUAUUUGCU  GUCAUACUAA  CUUGUAGGUU  CAUACGUAUG  1140

GCGACGGUUU  UUAUUGGCAC  CAGAUUCGAG  AUCCGUGAUG  CUAAUGGGAA  GGUCGUGGCU  1200

ACUGUACCAA  CUAGGAUCAA  AAAUGUUGCA  UUUGACUUCU  UCCAGAAGCU  AAAACAGUCA  1260

GGGGUGAGAG  UUGGAGUCAA  CGAAUUCGUU  GUUAUAAAAC  CAGGUGCAUU  AUGUGUCAUA  1320

GACACCCCUG  AAGGGAAAGG  AACAGGUUUC  UUUUCGGCA   AUGACAUAGU  AACAGCAGCA  1380

CAUGUUGUUG  GCAAUAAUAC  UUUUGUGAAU  GUGUGCUACG  AGGGCUUGAU  GUACGAAGCG  1440

AAAGUUCGUU  ACAUGCCUGA  AAAGGACAUA  GCAUUCAUAA  CUUGUCCUGG  UGACUUGCAU  1500

CCAACAGCAA  GAUUAAAAUU  AUCAAAGAAC  CCAGAUUAUA  GUUAUGUCAC  AGUCAUGGCU  1560

UACGUGAAUG  AAGAUCUUGU  GGUUUCAACC  GCAGCUGCCA  UGGUGCAUGG  UAACACUCUC  1620

UCAUAUGCAG  UUCGCACCCA  AGACGGGAUG  UCGGGUGCAC  CAGUUUGUGA  CAAGUAUGGU  1680

CGGGUGUUGG  CAGUCCAUCA  AACCAAUACU  GGUACACUG   GAGGUGCUGU  CAUAAUAGAC  1740

CCAGCAGACU  UUCAUCCAGU  GAAGGCCCCA  UCUCAGGUGG  AAUUGCUCAA  AGAGGAAAUA  1800

GAGCGACUAA  AAGCCCAAUU  GAAUUCCGCC  GCUGAGAACC  CAGCGACUGU  UGCUACACAA  1860

CAACCUGCCA  UUACAUUAGA  ACAGAAAAGU  GUUAGCGACA  GUGAUGUUGU  UGACCUUGUC  1920

AGAACUGCAA  UGGAACGUGA  GAUGAAGGUA  CUGCGUGAUG  AAAUCAAUGG  GAUACUUGCA  1980

CCAUUUCUAC  AAAAAAAGAA  AGGUAAGACC  AAGCAUGGUA  GGGUAGAGU   CAGACGUAAC  2040

CUUAGAAAAG  GCGUGAAACU  CCUUACUGAG  GAAGAGUAUC  GAGAACUCUU  AGAGAAAGGU  2100

CUAGAUCGUG  AGACAUUCCU  UGACCUUAUA  GACCGCAUUA  UUGGAGAGAG  GUCUGGCUAC  2160

CCUGACUAUG  AUGAUGAGGA  UUAUUAUGAU  GAAGAUGAUG  AUGGAUGGGG  AAUGGUUGGU  2220

GAUGAUGUAG  AAUUUGAUUA  UACUGAAGUA  AUUAAUUUUG  ACCAAGCAAA  ACCAACUCCU  2280

GCCCCAAGAA  CAACCAAGCC  AAAACCUUGC  CCCGAGCCAG  AAACUGAAAC  ACAACCACUU  2340

GAUUUGUCUC  AGAAGAAAGA  GAAACAACCA  GAACAUGAAC  AACAAGUGGU  GAAGUCUACC  2400

AAGCCUCAGA  AGAAUGAACC  UCAGCCAUAU  UCACAAACUU  AUGGCAAGGC  ACCAAUCUGG  2460

GAAUCUUAUG  AUUUUGACUG  GGACGAGGAU  GAUGCCAAGU  CAUCCUGCC   AGCACCACAC  2520

CGGUUAACUA  AGGCAGAUGA  AAUAGUUCUU  GGGUCAAAAA  UUGUCAAGCU  UAGGACGAUU  2580

AUUGAAACAG  CCAUUAAGAC  CCAGAACUAU  AGUGCACUAC  CUGAAGCUGU  GUUUGAGCUC  2640

GACAAAGCAG  CUUAUGAAGC  AGGUCUAGAA  GGUUUCCUCC  AAAGAGUUAA  AUCGAAAAAC  2700

AAGGCCCCAA  AAACUACAA   AGGGCCCCAG  AAGACCAAGG  GGCCCAAAAU  UAUCACUCAU  2760

UAGAUGCAUG  GAAAUCAUUG  CUAGAACCUC  CACGUGAGCG  GAGGUGCGUA  CCUGCUAAUU  2820

UUCCAUUGUU  AGGUCAUUUA  CCAAUUAAUA  GACCCAUCUU  UGAUGAUAAG  AAACCCAGGG  2880

AUGAUCUCCU  UGGAUUACUU  CCAGAACCAA  CCUGGCAUGC  UUUUGAGGAA  UAUGGACCAA  2940

CUACAUGGGG  CCCACAAGCU  UUCAUUAAGU  CUUUUGAUAA  AUUCUUUUAU  GCAGAACCAA  3000

UUGAUUUUUU  UUCAGAAUAU  CCACAGUUGU  GUGCUUUCGC  UGAUUGGGCA  ACUUAUCGCG  3060

AGUUUCGGUA  UCUAGAGGAC  ACUAGAGUGA  UACACAUAAC  UGCAACUGAG  AAGAAUACUG  3120

AUUCAACACC  UGCAUAUCCU  AAAAUGAAUU  AUUUUGAUAC  UGAAGAAAGU  UAUUUGGAAG  3180

CACAUGGGUG  GGCUCCAUAU  AUUAGAGAAU  UCACUAGGGU  CUUCAAAGGA  GACAAACCUG  3240
```

|  |  |  |  |  |  |  |
|---|---|---|---|---|---|---|
| AAGUACUGUG | GUACCUAUUU | CUUAAGAAAG | AGAUCAUUAA | GGAGGAAAAA | GUUAAAAAUU | 3300 |
| CUGAUAUCCG | GCAGAUAGUA | UGUGCCGAUC | CCAUUUACAC | CAGGAUAGGG | GCGUGCUUAG | 3360 |
| AGGCACAUCA | GAAUGCUUUG | AUGAAACAGC | AUACCGAUAC | UUCAGUUGGU | CAGUGUGGGU | 3420 |
| GGUCACCAAU | GGAAGCGGC | UUUAAAAAA | CAAUGCAACG | CCUAGUAAAU | AAAGGGAAUA | 3480 |
| AGUACUUUAU | UGAAUUUGAC | UGGACCCGCU | AUGAUGGAAC | UAUACCACCA | GCACUUUCA | 3540 |
| AACACAUCAA | AGAAAUUAGG | UGGAAUUUCA | UCAUAAAGA | CCAACGUGAA | AAGUACAGAC | 3600 |
| AUGUGCAUGA | CUGGUAUGUU | GACAACCUCC | UUAACCGCCA | UGUACUUCUA | CCAUCGGUG | 3660 |
| AAGUUACCUU | GCAGACACGA | GGCAAUCCAU | CUGGGCAGUU | UCAACAACA | AUGGAUAAUA | 3720 |
| ACAUGGUCAA | UUUUUGGCUA | CAAGCUUUUG | AGUUCGCUUA | UUUCAAUGGC | CCAGACAAAG | 3780 |
| ACCUUUGGAA | GACCUAUGAC | ACUGUGGUUU | AUGGAGAUGA | CAGGCUCUCU | ACAACACCUU | 3840 |
| CGGUACCUGA | UGAUUAUGAG | GAGAGAGUGA | UCACUAUGUA | UAGAGACAUC | UUUGGCAUGU | 3900 |
| GGGUUAAGCC | CGGGAAGGUC | AUCUGUAGAA | ACAGCAUAGU | UGGAUUAUCC | UUUUGUGGCU | 3960 |
| UUACUGUUAA | UGAAAAUCUU | GAACCUGUGC | CAACCUCUCC | GGAAAAGUUG | AUGGCAUCAC | 4020 |
| UGCUAAAGCC | UUAUAAAGUU | UUACCUGAUC | UUGAAUCACU | CCAUGGGAAG | CUCCUAUGCU | 4080 |
| AUCAGUUGCU | UGCUGCGUUC | AUGGCAGAAG | AUCACCCUUU | UAAGGUGUAU | AUAGAACACU | 4140 |
| GCCUAUCACG | GACUGCAAAG | CAGCUUCGUG | ACUCUGGCCU | ACCGGCCAGG | CUCACAGAAG | 4200 |
| AGCAACUCCA | UCGCAUUUGG | AGGGGAGGAC | CAAAGAAGUG | UGAUGGC |  | 4247 |

( 2 ) INFORMATION FOR SEQ ID NO:3:

( i ) SEQUENCE CHARACTERISTICS:
        ( A ) LENGTH: 2515 base pairs
        ( B ) TYPE: nucleic acid
        ( C ) STRANDEDNESS: single
        ( D ) TOPOLOGY: linear ( i i ) MOLECULE TYPE: RNA (genomic)

( i i i ) HYPOTHETICAL: NO ( i v ) ANTI-SENSE: NO ( v i ) ORIGINAL SOURCE:
        ( A ) ORGANISM: Human Astrovirus
        ( B ) STRAIN: Serotype 2

( x i ) SEQUENCE DESCRIPTION: SEQ ID NO:3:

|  |  |  |  |  |  |  |
|---|---|---|---|---|---|---|
| AAAGAAGUGU | GAUGGCUAGC | AAGUCUGACA | AGCAAGUCAC | UGUUGAGGUC | AAUAACAAUG | 60 |
| GCCGAAACAG | GAGCAAAUCC | AGAGCUCGAU | CACAAUCUAG | AGGUCGAGGU | AGAUCAGUCA | 120 |
| AAAUCACAGU | CAAUUCUCAC | AACAAAGGCA | GAAGACAAAA | CGGACGCAAC | AAAUAUCAAU | 180 |
| CUAAUCAGCG | UGUCCGUAAA | AUUGUCAAUA | ACAACUCAG | GAAACAGGGU | GUCACAGGAC | 240 |
| CAAAACCUGC | AAUAUGCCAG | AGAGCCACAG | CAACACUUGG | ACAAUUGGA | UCAAACACAA | 300 |
| CAGGAGCAAC | AGAGAUCGAG | GCGUGCAUAC | UCCUUAAUCC | CGUCCUGGUU | AAGGACGCUA | 360 |
| CUGGAAGUAC | UCAGUUGGG | CCAGUGCAGG | CGCUAGGUGC | UCAGUAUUCA | AUGUGGAAAC | 420 |
| UAAAGUAUUU | GAAUGUUAAA | CUGACUUCCA | UGGUGGGCGC | CUCAGCUGUU | AACGGGACUG | 480 |
| UACUCCGCAU | CUCGCUCAAC | CCUACAUCCA | CUCCAUCAUC | AACUAGCUGG | UCUGGACUUG | 540 |
| GUGCUCGUAA | GCACAUGGAU | GUUACAGUGG | GCAGGAAUGC | AGUCUUUAAA | CUUAGACCAU | 600 |
| CAGACCUUGG | AGGGCCAAGG | GAUGGCUGGU | GGCUCACUAA | UACCAAUGAC | AAUGCAUCUG | 660 |
| AUACAUUAGG | CCCAUCUAUU | GAAAUUCACA | CCCUUGGUAA | AACCAUGUCU | UCAUAUAAAA | 720 |
| AUGAGCAAUU | UACAGGUGGA | CUAUUUCUUG | UUGAGCUUGC | UUCAGAAUGG | UGUUUUACUG | 780 |

| | | | | | | |
|---|---|---|---|---|---|---|
| GCUAUGCAGC | UAAUCCAAAU | UUAGUUAAUU | UGGUUAAAUC | CACUGAUCAU | GAGGUGAAUG | 840 |
| UCACUUUUGA | GGGCUCAAAA | GGUACGCCCC | UAAUAAUGAA | UGUCGCAGAG | CACAGCCACU | 900 |
| UUGCAAGAAU | GGCUGAACAA | CAUUCCUCCA | UCUCAACAAC | AUUUUCAAGA | GCUGGAGGCG | 960 |
| AUGCAACAUC | UGACACUGUU | UGGCAGGUGC | UGAACACAGC | AGUCUCAGCA | GCAGAGCUUG | 1020 |
| UAGCCCCACC | ACCGUUCAAU | UGGCUUAUAA | AGGGUGGCUG | GUGGUUUGUA | AAGUUGAUUG | 1080 |
| CAGGUAGAAC | UAGAACUGGU | ACCAAGCAAU | UUUAUGUUUA | UCCUAGUUAU | CAGGAUGCUU | 1140 |
| UAUCAAAUAA | ACCAGCUCUU | UGCACUGGUG | GAGUUACAGG | UGGCGUUCUA | CGUACCACAC | 1200 |
| CGGUAACAAC | UCUACAGUUC | ACUCAAAUGA | ACCAGCCAAG | CCUUGGGCAU | GGUGAGCACA | 1260 |
| CUGCCACCAU | UGGCAGUAUU | GUGCAAGAUC | CAAGUGGGGA | ACUGCGUGUG | CUGCUAACAG | 1320 |
| UUGGCUCAAU | CAUGAGCCCG | AAUUCAGCUG | AUAGGCAAGU | UGGCUGAAC | AAAACUCUGA | 1380 |
| CAGCGCCAGG | AACAAAUUCA | AAUGACAAUC | UUGUAAAGAU | AGCCCACGAC | UUGGGUCACU | 1440 |
| AUUUGAUCAU | GCAAGGGUUU | AUGCAUAUAA | AGACAGUAGA | GUGGUAUACU | CCUGAUUUUC | 1500 |
| AACCUUCGCG | UGACCCAACC | CCUAUUGCUG | GCAUGUCAGU | GAUGGUUAAC | AUAACAAAGA | 1560 |
| AGGCUGAUGU | CUACUUCAUG | AAGCAAUUCA | AAAAUUCUUA | CACCAACAAC | CGCCAUCAAA | 1620 |
| UAACAAGCAU | CUUUUUAAUU | AAACCAUUGG | CAGAUUUUAA | GGUGCAAUGU | AUAUGAGCU | 1680 |
| ACUUUAAAAG | AGAGUCACAU | GACAAUGAUG | GGGUUGCCAA | UCUUACAGUG | AGAAGUAUGA | 1740 |
| CCAGCCCGGA | GACUAUCAGG | UUUCAAGUUG | GAGAAUGGUA | UUUGCUAACA | AGUACCACAC | 1800 |
| UUAAGGAGAA | CAACCUACCA | GAGGGCUGGG | UUUGGGAUAG | GGUGGAGCUU | AAGAGUGACA | 1860 |
| CACCAUACUA | UGCUGAUCAA | GCAUUGACAU | AUUUCAUAAC | ACCACCCCA | GUGGACUCCC | 1920 |
| AAAUUUUAUU | UGAAGGUAAC | ACCACAUUGC | CCAGAAUUUC | CUCUCCGCCU | GACAAUCCCA | 1980 |
| GCGGGCGAUA | UAUGGAAAGC | CACCAGCAAG | ACUGUGACUC | UUCUGAUGAU | GAGGAUGAUU | 2040 |
| GUGAAAAUGU | UUCAGAGGAG | ACAGAAACUG | AGGAUGAGGA | AGAUGAGGAC | GAAGACGAUG | 2100 |
| AAGCGGACAG | GUUUGAUCUC | CACAGCCCCU | AUAGUUCUGA | ACCUGAGGAC | UCUGAUGAGA | 2160 |
| ACAACCGUGU | AACCCUCCUC | UCUACACUCA | UAAACCAAGG | AAUGACAGUG | GAGCGCGCAA | 2220 |
| CAAGAAUAAC | UAAACGCGCU | UUCCCAACCU | GCGCUGAGAA | ACUGAAGCGC | AGCGUGUACA | 2280 |
| UGGACCUGCU | UGCCUCCGGU | GCAUCGCCGA | GCAGUGCAUG | GUCAAACGCG | UGUGAUGAAG | 2340 |
| CACGCAAUGU | GGGCAGCAAU | CAGCUGGCCA | AACUUCUGG | AGACCGCGGC | CACGCCGAGU | 2400 |
| AGGAUCGAGG | GUACAGUCUC | CAUUACUUUU | CUGUCUCUGU | UUAGAUUAUU | UUAAUCACCA | 2460 |
| UUUAAAAUUG | AUUUAAUCAG | AAGCAAAAAA | AAAAAAAAA | AAAAAAAAA | AAAAA | 2515 |

( 2 ) INFORMATION FOR SEQ ID NO:4:

( i ) SEQUENCE CHARACTERISTICS:
        ( A ) LENGTH: 1416 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Human Astrovirus
        ( B ) STRAIN: Serotype 2

( x i ) SEQUENCE DESCRIPTION: SEQ ID NO:4:

```
Met Ala His Gly Glu Pro Tyr Tyr Ser Ser Lys Pro Asp Lys Asp Phe
1               5                   10                  15

Asn Phe Gly Ser Thr Met Ala Arg Arg Gln Met Thr Pro Thr Met Val
        20                  25              30

Thr Lys Leu Pro Lys Phe Val Arg Asn Ser Pro Gln Ala Tyr Asp Trp
        35                  40                  45

Ile Val Arg Gly Leu Ile Phe Pro Thr Thr Gly Lys Thr Tyr Phe Gln
50                  55                  60

Arg Val Val Val Ile Thr Gly Leu Glu Asp Gly Thr Tyr Gly Ser
65                  70                  75                  80

Phe Ala Phe Asp Gly Arg Glu Trp Val Glu Ile Tyr Pro Ile Glu His
                85                  90                  95

Leu Asn Leu Met Ser Ser Leu Lys Leu Ile His Lys Ala Asn Ala Leu
            100                 105                 110

Gln Glu Arg Leu Arg Leu Ser Gln Glu Lys Ala Thr Leu Ala Leu
            115                 120                 125

Asp Val Gln Phe Leu Gln His Glu Asn Val Arg Leu Lys Glu Leu Ile
        130                 135                 140

Pro Lys Pro Glu Pro Arg Lys Ile Gln Met Lys Trp Ile Ile Val Gly
145                 150                 155                 160

Ala Val Leu Thr Phe Leu Ser Leu Ile Pro Gly Gly Tyr Ala Gln Ser
                165                 170                 175

Gln Thr Asn Asn Thr Ile Phe Thr Asp Val Ile Ala Ala Cys Lys Tyr
            180                 185                 190

Ser Thr Glu Thr Leu Thr Glu Asn Leu Asp Leu Arg Ile Lys Leu Ala
        195                 200                 205

Leu Ala Asn Ile Thr Ile Ser Asp Lys Leu Asp Ala Val Arg Gln Ile
210                 215                 220

Leu Asn Phe Ala Phe Val Pro Arg Ala His Trp Leu Arg Thr Val Phe
225                 230                 235                 240

Tyr Tyr Ile His Tyr Tyr Glu Met Trp Asn Ile Phe Met Phe Val Leu
                245                 250                 255

Ala Ile Gly Thr Val Met Arg Ser Ala Arg Pro Gly Thr Asp Leu Ile
            260                 265                 270

Thr Leu Ala Thr Ser His Leu Ser Gly Phe Arg Leu Ala Val Leu Pro
        275                 280                 285

Thr Ile Pro Phe His Thr Thr Met Thr Leu Trp Val Met Asn Thr Leu
290                 295                 300

Met Val Cys Tyr Tyr Phe Asp Asn Leu Leu Ala Ile Thr Met Ala Ile
305                 310                 315                 320

Leu Ala Pro Ile Leu Gly Ile Ile Phe Leu Cys Phe Met Glu Asp Ser
                325                 330                 335

Asn Tyr Val Ser Gln Ile Arg Gly Leu Ile Ala Thr Ala Ile Leu Ile
            340                 345                 350

Ala Gly Gly His Ala Cys Leu Thr Leu Thr Gly Thr Thr Thr Ser Leu
        355                 360                 365

Phe Ala Val Ile Leu Thr Cys Arg Phe Ile Arg Met Ala Thr Val Phe
        370                 375                 380

Ile Gly Thr Arg Phe Glu Ile Arg Asp Ala Asn Gly Lys Val Val Ala
385                 390                 395                 400

Thr Val Pro Thr Arg Ile Lys Asn Val Ala Phe Asp Phe Phe Gln Lys
                405                 410                 415

Leu Lys Gln Ser Gly Val Arg Val Gly Val Asn Glu Phe Val Val Ile
            420                 425                 430
```

-continued

```
Lys  Pro  Gly  Ala  Leu  Cys  Val  Ile  Asp  Thr  Pro  Glu  Gly  Lys  Gly  Thr
          435                      440                     445

Gly  Phe  Phe  Ser  Gly  Asn  Asp  Ile  Val  Thr  Ala  Ala  His  Val  Val  Gly
     450                      455                     460

Asn  Asn  Thr  Phe  Val  Asn  Val  Cys  Tyr  Glu  Gly  Leu  Met  Tyr  Glu  Ala
465                      470                     475                      480

Lys  Val  Arg  Tyr  Met  Pro  Glu  Lys  Asp  Ile  Ala  Phe  Ile  Thr  Cys  Pro
               485                      490                     495

Gly  Asp  Leu  His  Pro  Thr  Ala  Arg  Leu  Lys  Leu  Ser  Lys  Asn  Pro  Asp
               500                      505                     510

Tyr  Ser  Tyr  Val  Thr  Val  Met  Ala  Tyr  Val  Asn  Glu  Asp  Leu  Val  Val
               515                      520                     525

Ser  Thr  Ala  Ala  Ala  Met  Val  His  Gly  Asn  Thr  Leu  Ser  Tyr  Ala  Val
     530                      535                     540

Arg  Thr  Gln  Asp  Gly  Met  Ser  Gly  Ala  Pro  Val  Cys  Asp  Lys  Tyr  Gly
545                      550                     555                      560

Arg  Val  Leu  Ala  Val  His  Gln  Thr  Asn  Thr  Gly  Tyr  Thr  Gly  Gly  Ala
               565                      570                     575

Val  Ile  Ile  Asp  Pro  Ala  Asp  Phe  His  Pro  Val  Lys  Ala  Pro  Ser  Gln
               580                      585                     590

Val  Glu  Leu  Leu  Lys  Glu  Glu  Ile  Glu  Arg  Leu  Lys  Ala  Gln  Leu  Asn
               595                      600                     605

Ser  Ala  Ala  Glu  Asn  Pro  Ala  Thr  Val  Ala  Thr  Gln  Gln  Pro  Ala  Ile
     610                      615                     620

Thr  Leu  Glu  Gln  Lys  Ser  Val  Ser  Asp  Ser  Asp  Val  Val  Asp  Leu  Val
625                      630                     635                      640

Arg  Thr  Ala  Met  Glu  Arg  Glu  Met  Lys  Val  Leu  Arg  Asp  Glu  Ile  Asn
               645                      650                     655

Gly  Ile  Leu  Ala  Pro  Phe  Leu  Gln  Lys  Lys  Lys  Gly  Lys  Thr  Lys  His
               660                      665                     670

Gly  Arg  Gly  Arg  Val  Arg  Arg  Asn  Leu  Arg  Lys  Gly  Val  Lys  Leu  Leu
               675                      680                     685

Thr  Glu  Glu  Glu  Tyr  Arg  Glu  Leu  Leu  Glu  Lys  Gly  Leu  Asp  Arg  Glu
     690                      695                     700

Thr  Phe  Leu  Asp  Leu  Ile  Asp  Arg  Ile  Ile  Gly  Glu  Arg  Ser  Gly  Tyr
705                      710                     715                      720

Pro  Asp  Tyr  Asp  Asp  Glu  Asp  Tyr  Tyr  Asp  Glu  Asp  Asp  Asp  Gly  Trp
                    725                     730                     735

Gly  Met  Val  Gly  Asp  Asp  Val  Glu  Phe  Asp  Tyr  Thr  Glu  Val  Ile  Asn
               740                      745                     750

Phe  Asp  Gln  Ala  Lys  Pro  Thr  Pro  Ala  Pro  Arg  Thr  Thr  Lys  Pro  Lys
          755                      760                     765

Pro  Cys  Pro  Glu  Pro  Glu  Thr  Glu  Thr  Gln  Pro  Leu  Asp  Leu  Ser  Gln
     770                      775                     780

Lys  Lys  Glu  Lys  Gln  Pro  Glu  His  Glu  Gln  Gln  Val  Val  Lys  Ser  Thr
785                      790                     795                      800

Lys  Pro  Gln  Lys  Asn  Glu  Pro  Gln  Pro  Tyr  Ser  Gln  Thr  Tyr  Gly  Lys
                    805                     810                     815

Ala  Pro  Ile  Trp  Glu  Ser  Tyr  Asp  Phe  Asp  Trp  Asp  Glu  Asp  Asp  Ala
               820                      825                     830

Lys  Phe  Ile  Leu  Pro  Ala  Pro  His  Arg  Leu  Thr  Lys  Ala  Asp  Glu  Ile
          835                      840                     845
```

```
Val Leu Gly Ser Lys Ile Val Lys Leu Arg Thr Ile Ile Glu Thr Ala
    850             855             860
Ile Lys Thr Gln Asn Tyr Ser Ala Leu Pro Glu Ala Val Phe Glu Leu
865             870             875             880
Asp Lys Ala Ala Tyr Glu Ala Gly Leu Gly Phe Leu Gln Arg Val
            885             890             895
Lys Ser Lys Asn Lys Ala Pro Lys Lys Leu Gln Arg Ala Pro Glu Asp
            900             905             910
Gln Gly Ala Gln Asn Tyr His Ser Leu Asp Ala Trp Lys Ser Leu Leu
            915             920             925
Glu Pro Pro Arg Glu Arg Arg Cys Val Pro Ala Asn Phe Pro Leu Leu
            930             935             940
Gly His Leu Pro Ile Asn Arg Pro Ile Phe Asp Asp Lys Lys Pro Arg
945             950             955             960
Asp Asp Leu Leu Gly Leu Leu Pro Glu Pro Thr Trp His Ala Phe Glu
            965             970             975
Glu Tyr Gly Pro Thr Thr Trp Gly Pro Gln Ala Phe Ile Lys Ser Phe
            980             985             990
Asp Lys Phe Phe Tyr Ala Glu Pro Ile Asp Phe Phe Ser Glu Tyr Pro
            995             1000            1005
Gln Leu Cys Ala Phe Ala Asp Trp Ala Thr Tyr Arg Glu Phe Arg Tyr
1010            1015            1020
Leu Glu Asp Thr Arg Val Ile His Ile Thr Ala Thr Glu Lys Asn Thr
1025            1030            1035            1040
Asp Ser Thr Pro Ala Tyr Pro Lys Met Asn Tyr Phe Asp Thr Glu Glu
            1045            1050            1055
Ser Tyr Leu Glu Ala His Gly Trp Ala Pro Tyr Ile Arg Glu Phe Thr
            1060            1065            1070
Arg Val Phe Lys Gly Asp Lys Pro Glu Val Leu Trp Tyr Leu Phe Leu
            1075            1080            1085
Lys Lys Glu Ile Ile Lys Glu Lys Val Lys Asn Ser Asp Ile Arg
            1090            1095            1100
Gln Ile Val Cys Ala Asp Pro Ile Tyr Thr Arg Ile Gly Ala Cys Leu
1105            1110            1115            1120
Glu Ala His Gln Asn Ala Leu Met Lys Gln His Thr Asp Thr Ser Val
            1125            1130            1135
Gly Gln Cys Gly Trp Ser Pro Met Glu Gly Gly Phe Lys Lys Thr Met
            1140            1145            1150
Gln Arg Leu Val Asn Lys Gly Asn Lys Tyr Phe Ile Glu Phe Asp Trp
            1155            1160            1165
Thr Arg Tyr Asp Gly Thr Ile Pro Pro Ala Leu Phe Lys His Ile Lys
            1170            1175            1180
Glu Ile Arg Trp Asn Phe Ile Asn Lys Asp Gln Arg Glu Lys Tyr Arg
1185            1190            1195            1200
His Val His Asp Trp Tyr Val Asp Asn Leu Leu Asn Arg His Val Leu
            1205            1210            1215
Leu Pro Ser Gly Glu Val Thr Leu Gln Thr Arg Gly Asn Pro Ser Gly
            1220            1225            1230
Gln Phe Ser Thr Thr Met Asp Asn Asn Met Val Asn Phe Trp Leu Gln
            1235            1240            1245
Ala Phe Glu Phe Ala Tyr Phe Asn Gly Pro Asp Lys Asp Leu Trp Lys
            1250            1255            1260
Thr Tyr Asp Thr Val Val Tyr Gly Asp Asp Arg Leu Ser Thr Thr Pro
1265            1270            1275            1280
```

|     |     |     |     |     |     |     |     |     |     |     |     |     |     |     |
|---|---|---|---|---|---|---|---|---|---|---|---|---|---|---|
| Ser | Val | Pro | Asp | Asp<br>1285 | Tyr | Glu | Glu | Arg | Val<br>1290 | Ile | Thr | Met | Tyr | Arg Asp<br>1295 |
| Ile | Phe | Gly | Met<br>1300 | Trp | Val | Lys | Pro | Gly<br>1305 | Lys | Val | Ile | Cys | Arg<br>1310 | Asn Ser |
| Ile | Val | Gly<br>1315 | Leu | Ser | Phe | Cys | Gly<br>1320 | Phe | Thr | Val | Asn | Glu<br>1325 | Asn | Leu Glu |
| Pro | Val<br>1330 | Pro | Thr | Ser | Pro | Glu<br>1335 | Lys | Leu | Met | Ala | Ser<br>1340 | Leu | Leu | Lys Pro |
| Tyr<br>1345 | Lys | Val | Leu | Pro | Asp<br>1350 | Leu | Glu | Ser | Leu | His<br>1355 | Gly | Lys | Leu | Leu Cys<br>1360 |
| Tyr | Gln | Leu | Leu | Ala<br>1365 | Ala | Phe | Met | Ala | Glu<br>1370 | Asp | His | Pro | Phe | Lys Val<br>1375 |
| Tyr | Ile | Glu | His<br>1380 | Cys | Leu | Ser | Arg | Thr<br>1385 | Ala | Lys | Gln | Leu | Arg<br>1390 | Asp Ser |
| Gly | Leu | Pro<br>1395 | Ala | Arg | Leu | Thr | Glu<br>1400 | Glu | Gln | Leu | His | Arg<br>1405 | Ile | Trp Arg |
| Gly | Gly | Pro<br>1410 | Lys | Lys | Cys | Asp<br>1415 | Gly |     |     |     |     |     |     |     |

What is claimed is:

1. An isolated nucleic acid encoding human Astrovirus serotype 2 as set forth in the Sequencing Listing as SEQ ID NO: 1.

2. An isolated nucleic acid encoding open reading frame 1a of human Astrovirus serotype 2, consisting of nucleotides 83 through 2,842 contained in the nucleotide sequence as set forth in the Sequencing Listing as SEQ ID NO: 1.

3. An isolated nucleic acid encoding open reading frame 1b of human Astrovirus serotype 2, consisting of nucleotides 2,773 through 4,329 contained in the nucleotide sequence as set forth in the Sequencing Listing as SEQ ID NO: 1.

4. An isolated nucleic acid encoding open reading frame 2 of human Astrovirus serotype 2, consisting of nucleotides 4325 through 6712 contained in the nucleotide sequence as set forth in the Sequencing Listing as SEQ ID NO: 1.

5. An isolated nucleic acid encoding open reading frame 1a/1b of human Astrovirus serotype 2, consisting of the nucleotide sequence as set forth in the Sequencing Listing as SEQ ID NO: 2.

6. An isolated nucleic acid encoding subgenomic RNA of human Astrovirus serotype 2, consisting of the nucleotide sequence as set forth in the Sequencing Listing as SEQ ID NO: 3.

7. A vector comprising the nucleic acid of claim 1.

8. The vector of claim 7 in a host that expresses the polypeptide encoded by the nucleic acid.

* * * * *

UNITED STATES PATENT AND TRADEMARK OFFICE
CERTIFICATE OF CORRECTION

PATENT NO.   : 5,625,049
DATED        : April 29, 1997
INVENTOR(S)  : Stephan S. Monroe, Roger I. Glass, Marion Koopmans, Baoming Jiang It is certified that error appears in the above-identified patent and that said Letters Patent is hereby corrected as shown below:

[73]   Assignee: The Government of the United States of America as represented by the Secretary, Dept. of Health and Human Services, Rockville, Maryland (US)

Signed and Sealed this

Thirty-first Day of July, 2001

Attest:

NICHOLAS P. GODICI
*Attesting Officer*   *Acting Director of the United States Patent and Trademark Office*